(12) United States Patent
Lyke et al.

(10) Patent No.: US 11,745,058 B2
(45) Date of Patent: *Sep. 5, 2023

(54) METHODS AND APPARATUS FOR COACHING BASED ON WORKOUT HISTORY

(71) Applicant: MYFITNESSPAL, INC., San Francisco, CA (US)

(72) Inventors: James Lyke, Austin, TX (US); Ben Hamill, Austin, TX (US); Jeff Knight, Austin, TX (US); Scott Laing, Austin, TX (US)

(73) Assignee: MyFitnessPal, Inc., Austin, TX (US)

( * ) Notice: Subject to any disclaimer, the term of this patent is extended or adjusted under 35 U.S.C. 154(b) by 791 days.

This patent is subject to a terminal disclaimer.

(21) Appl. No.: 16/588,199

(22) Filed: Sep. 30, 2019

(65) Prior Publication Data

US 2021/0093919 A1 Apr. 1, 2021

(51) Int. Cl.

| | |
|---|---|
| *G06F 7/00* | (2006.01) |
| *A63B 24/00* | (2006.01) |
| *A63B 71/06* | (2006.01) |
| *G06N 20/00* | (2019.01) |
| *G06F 16/9035* | (2019.01) |
| *G06F 16/906* | (2019.01) |
| *G16H 20/30* | (2018.01) |

(52) U.S. Cl.
CPC ...... *A63B 24/0075* (2013.01); *A63B 24/0062* (2013.01); *A63B 71/0622* (2013.01); *G06F 16/906* (2019.01); *G06F 16/9035* (2019.01); *G06N 20/00* (2019.01); *G16H 20/30* (2018.01); *A63B 2024/0068* (2013.01)

(58) Field of Classification Search
CPC ...... G06N 50/003; G06N 20/00; G16H 15/00; G16H 10/20; G16H 40/63; G16H 40/67; G06F 16/9035; G06F 16/906; A63B 24/0075; A63B 24/0062; A63B 71/0622; A63B 2024/0068
See application file for complete search history.

(56) References Cited

U.S. PATENT DOCUMENTS

| | | | |
|---|---|---|---|
| 8,690,578 B1 * | 4/2014 | Nusbaum ........... | G09B 19/0092 705/2 |
| 9,474,934 B1 * | 10/2016 | Krueger ............... | A61B 5/4872 |
| 9,691,023 B2 | 6/2017 | Barnes et al. | |
| 9,728,102 B2 * | 8/2017 | Nusbaum ............... | G16H 20/60 |

(Continued)

*Primary Examiner* — Mohammed R Uddin
(74) *Attorney, Agent, or Firm* — Maginot, Moore & Beck, LLP

(57) ABSTRACT

System and method for coaching based on workout history. Improved solutions enable intelligent management of a user's personal fitness journey based on workout recommendations that closely align with the user's traits. In one exemplary embodiment, workout data for a population of different individuals is analyzed to identify groups of similarly performing individuals. Each group of individuals is analyzed to generate an expected profile that approximates the physiological and/or psychological traits of the group. An expected profile includes heuristics and/or performance metrics that enable dynamic coaching during workouts. Subsequently thereafter, user's can be dynamically coached by their client device, based on the expected profile.

18 Claims, 10 Drawing Sheets

(56) References Cited

U.S. PATENT DOCUMENTS

| | | | |
|---|---|---|---|
| 9,886,871 B1* | 2/2018 | Rauhala | G09B 19/0038 |
| 10,065,074 B1 | 9/2018 | Hoang et al. | |
| 10,857,426 B1* | 12/2020 | Neumann | G06K 9/6276 |
| 11,316,941 B1* | 4/2022 | Jain | H04L 67/535 |
| 11,331,268 B2* | 5/2022 | Nguyen | A61K 9/2068 |
| 11,331,538 B2* | 5/2022 | Ward | A63B 21/153 |
| 2003/0204412 A1* | 10/2003 | Brier | G16H 20/30 |
| | | | 705/2 |
| 2005/0113650 A1 | 5/2005 | Pacione et al. | |
| 2006/0229163 A1* | 10/2006 | Waters | A63F 13/22 |
| | | | 482/8 |
| 2007/0219059 A1* | 9/2007 | Schwartz | A61B 5/02405 |
| | | | 482/8 |
| 2007/0232455 A1* | 10/2007 | Hanoun | A63B 24/0084 |
| | | | 482/8 |
| 2008/0214905 A1 | 9/2008 | Francescato et al. | |
| 2008/0300914 A1* | 12/2008 | Karkanias | A63B 71/0622 |
| | | | 705/2 |
| 2009/0069156 A1 | 3/2009 | Kurunmäki et al. | |
| 2011/0281687 A1* | 11/2011 | Gilley | A63B 24/0087 |
| | | | 482/8 |
| 2014/0228988 A1* | 8/2014 | Hoffman | A61B 5/6807 |
| | | | 700/91 |
| 2015/0126826 A1* | 5/2015 | Kaleal, III | A63B 24/00 |
| | | | 600/300 |
| 2015/0251074 A1 | 9/2015 | Ahmed et al. | |
| 2016/0086500 A1* | 3/2016 | Kaleal, III | A61B 5/43 |
| | | | 434/257 |
| 2016/0220867 A1* | 8/2016 | Flaherty | G16H 20/30 |
| 2017/0084196 A1* | 3/2017 | Nusbaum | G16H 20/30 |
| 2017/0216671 A1* | 8/2017 | Wisbey | A61B 5/02438 |
| 2017/0263147 A1* | 9/2017 | King | G11B 27/026 |
| 2017/0319904 A1* | 11/2017 | Deochand | G06Q 10/00 |
| 2017/0329933 A1 | 11/2017 | Brust et al. | |
| 2018/0126222 A1* | 5/2018 | Duale | G06Q 10/02 |
| 2018/0361203 A1* | 12/2018 | Wang | G06N 20/00 |
| 2019/0184234 A1* | 6/2019 | Packles | A63B 24/0075 |
| 2021/0050086 A1* | 2/2021 | Rose | G16H 10/60 |
| 2021/0354023 A1* | 11/2021 | Sinclair | A63B 24/0006 |
| 2021/0394011 A1* | 12/2021 | Neuhaus | A63B 24/0087 |
| 2021/0402259 A1* | 12/2021 | Belson | A63B 24/0087 |
| 2022/0023739 A1* | 1/2022 | DeGooyer | G06N 3/02 |
| 2022/0118340 A1* | 4/2022 | Putnam | G09B 19/00 |
| 2022/0125354 A1* | 4/2022 | Shen | G16H 50/30 |
| 2022/0133194 A1* | 5/2022 | Bach | A61B 5/0816 |
| | | | 600/544 |

* cited by examiner

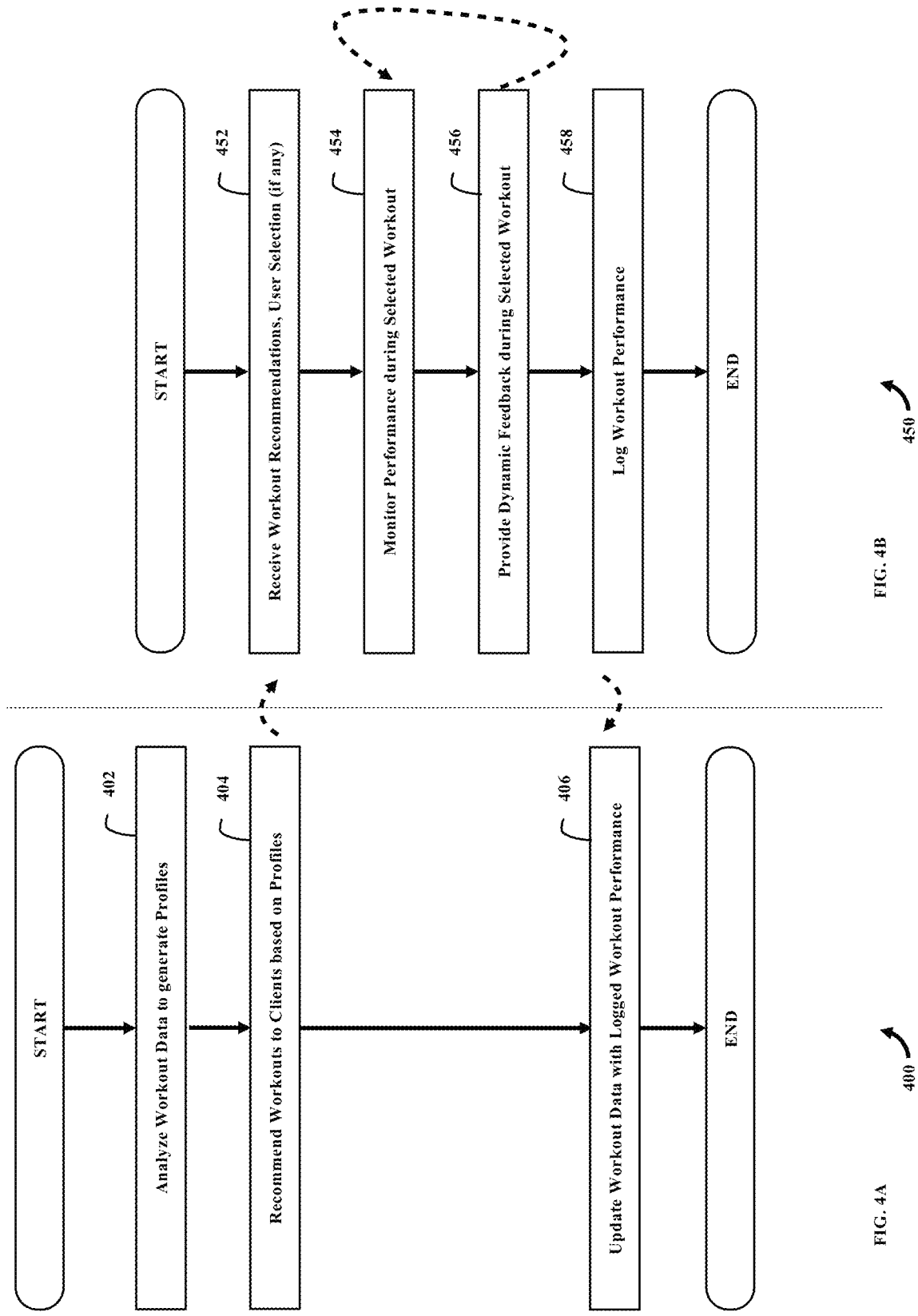

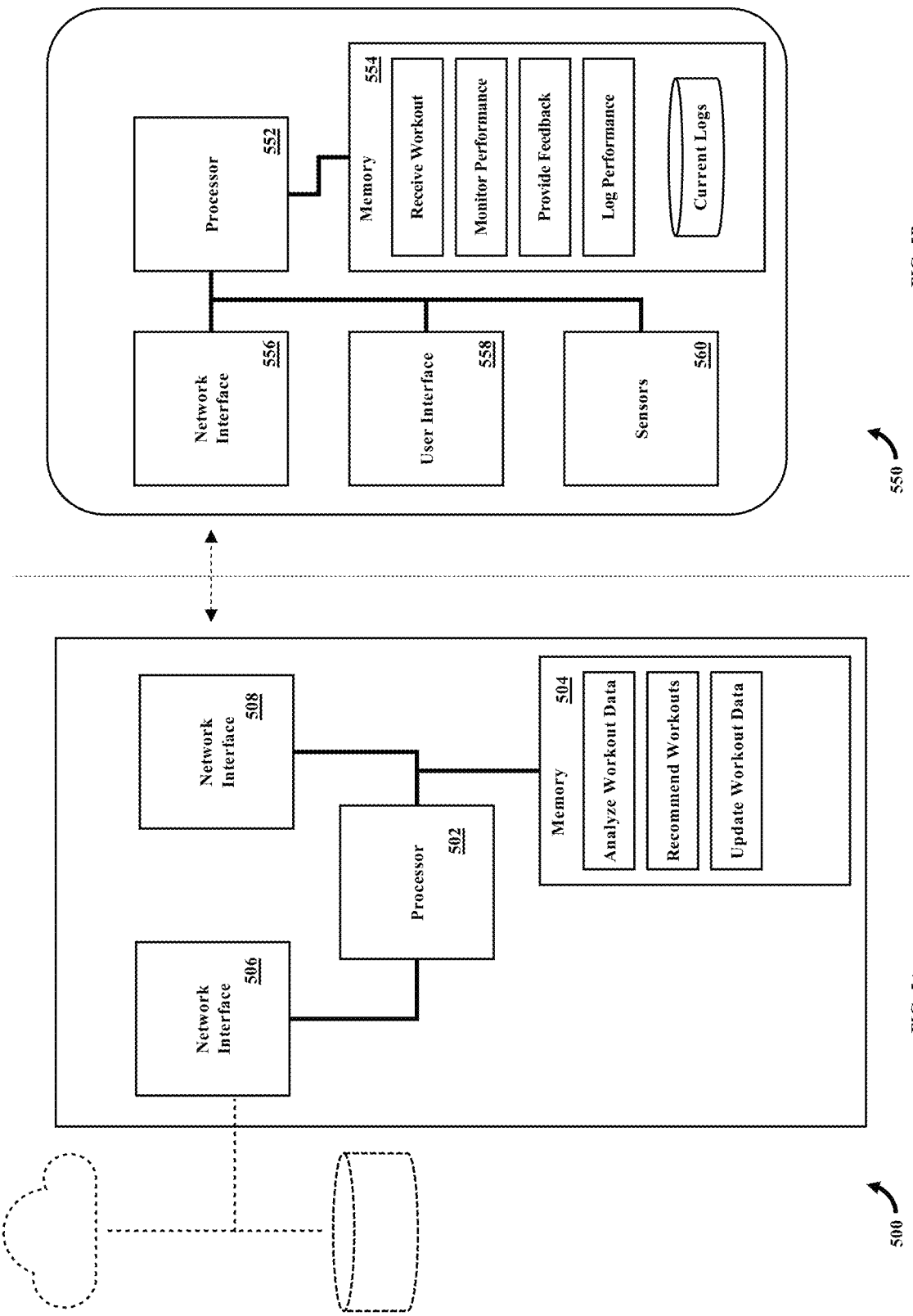

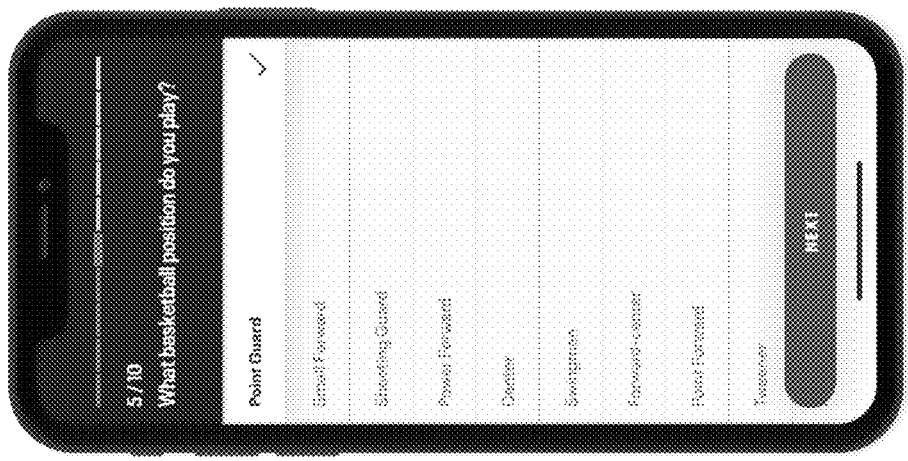
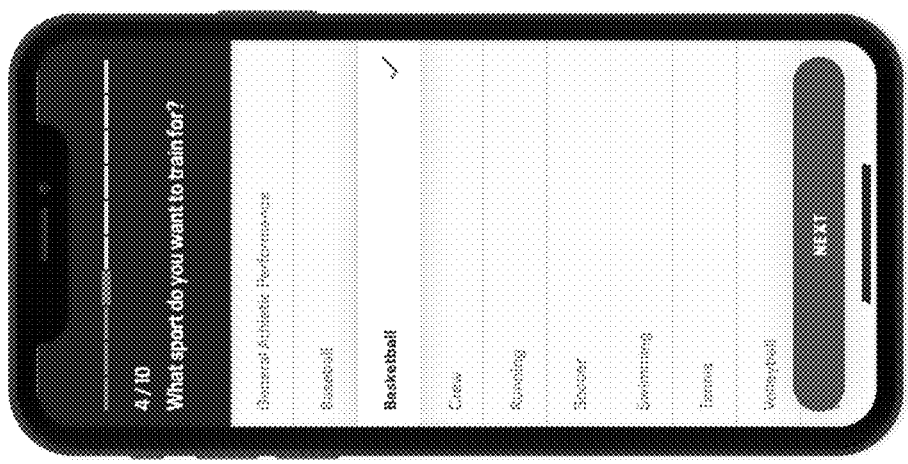
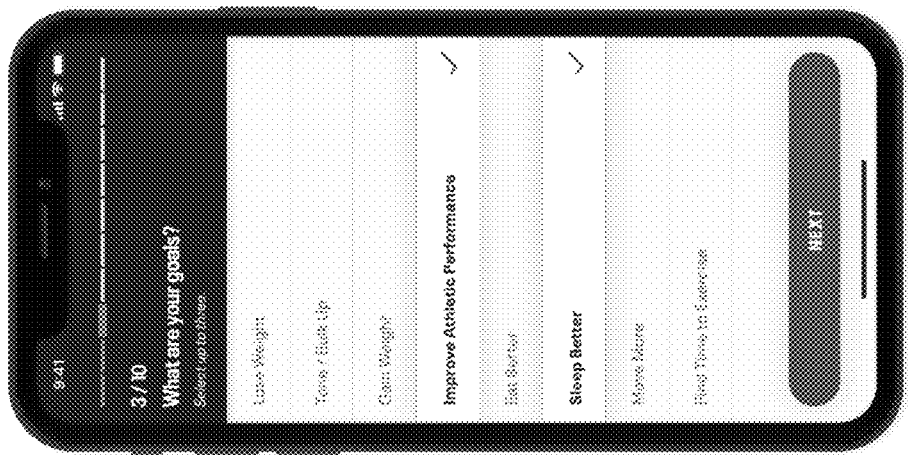
FIG. 6A

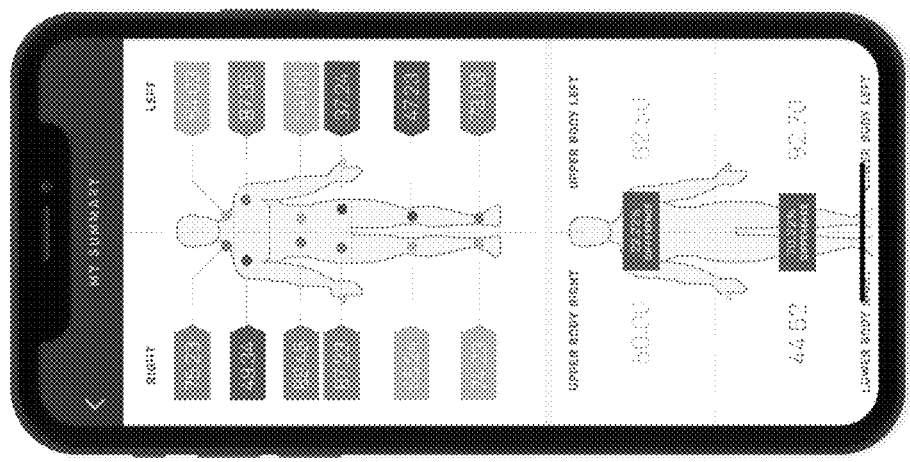
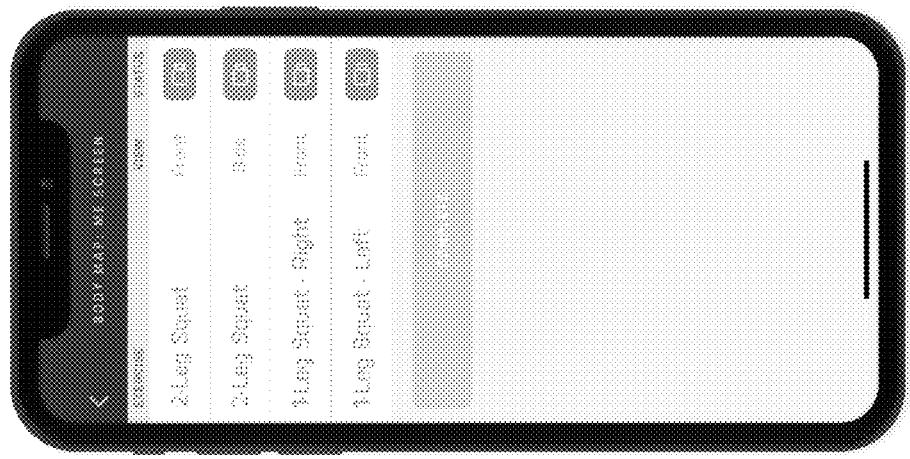
FIG. 6B

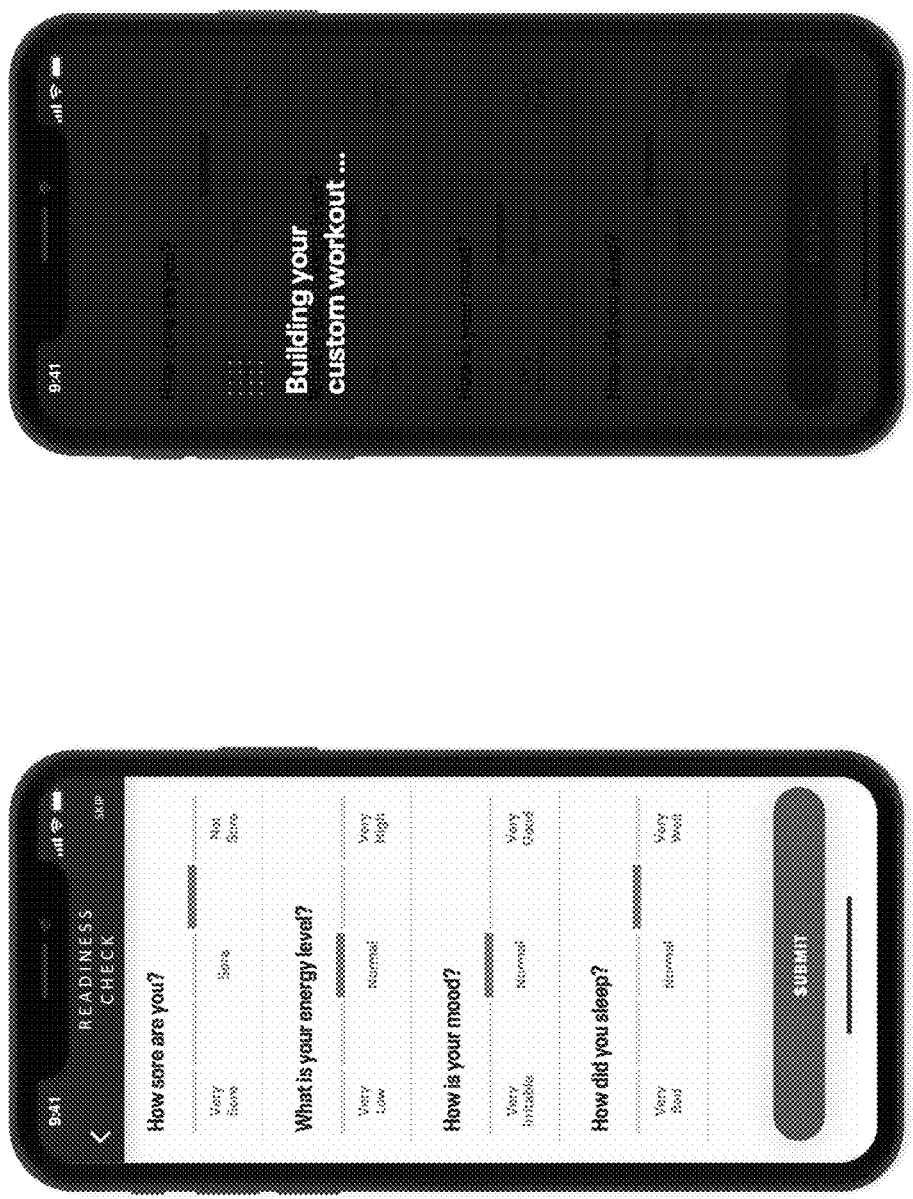

METHODS AND APPARATUS FOR COACHING BASED ON WORKOUT HISTORY

COPYRIGHT

A portion of the disclosure of this patent document contains material that is subject to copyright protection. The copyright owner has no objection to the facsimile reproduction by anyone of the patent document or the patent disclosure, as it appears in the Patent and Trademark Office patent files or records, but otherwise reserves all copyright rights whatsoever.

TECHNICAL FIELD

This disclosure relates generally to the field of personal fitness. More particularly, the present disclosure relates to systems, computer programs, devices, and methods for coaching a user based on workout history and/or personal fitness goals.

DESCRIPTION OF RELATED TECHNOLOGY

In recent years, health and fitness tracking applications that track user workouts and activities have become very popular. Routine physical activity is important to a healthy lifestyle and is known to prevent and/or ameliorate various health conditions, such as diabetes and obesity. Health and fitness tracking applications allow users to set and achieve personalized health goals by tracking the amount of physical activity, regularity of physical activity, and/or intensity of physical activity. These applications enable users to gain insights regarding their workout regimen efficacy.

However, existing health and fitness tracking applications often suggest workout routines based on generalizations of the human body and/or assumptions about workout performance. Hence what is needed are improved methods for providing workout recommendations and coaching.

SUMMARY

The present disclosure addresses the foregoing needs by disclosing, inter alia, methods, devices, systems, and computer programs for coaching a user based on workout history and/or personal fitness goals, thereby providing improved workout recommendations and coaching.

In one aspect, a method for enabling dynamic coaching feedback at a client device is disclosed. In one embodiment, the method includes: analyzing workout data records to create an expected profile; recommending a workout for a user based on the expected profile; wherein the expected profile includes at least one heuristic for generating dynamic feedback with the workout; and updating a user data record based on a logged performance corresponding to the workout.

In one variant, the workout data records are obtained from a population of users. In one such variant, the population of users are categorized based on at least one physiological or psychological trait.

In another variant, the expected profile includes an expected performance for a first exercise of the workout. In one such variant, the at least one heuristic for generating the dynamic feedback includes a rule for modifying a second exercise of the workout based on an actual performance of the first exercise of the workout. In another such variant, the at least one heuristic for generating the dynamic feedback includes a rule for motivating the user based on an actual performance of the first exercise of the workout.

In one variant, the method further includes identifying the expected profile from a plurality of expected profiles based on an assessment performance.

In another aspect, a health tracking server configured to recommend workouts to users is disclosed. In one embodiment, the health tracking server includes: a network interface; a processor; and a non-transitory computer-readable medium comprising one or more instructions. In one exemplary embodiment, the one or more instructions when executed by the processor, cause the health tracking server to: obtain workout data records associated with users; analyze the workout data records to group the users into subsets; analyze each subset to generate a corresponding profile comprising at least a heuristic and a performance metric associated therewith; match a first user with a first profile; and recommend a first workout to the first user based on the first profile.

In one variant, the users are grouped into the subsets based on machine learning data analysis of physiological or psychological traits.

In another variant, the corresponding profile for each subset is generated based on machine learning data analysis of physiological or psychological traits.

In another variant, the first user is matched with the first profile from a plurality of profiles based on an assessment exercise.

In another variant, the first user is matched with the first profile from a plurality of profiles based on a history of user workout data records.

In another variant, the first user is matched with the first profile from a plurality of profiles based on a fitness goal identified by the first user.

In another variant, the first workout is recommended responsive to user input.

In another aspect, a user apparatus is disclosed. In one embodiment, the user apparatus includes: a user interface; a network interface; a processor; and a non-transitory computer-readable medium. In one exemplary embodiment, the one or more instructions when executed by the processor, cause the user apparatus to: receive a recommended workout and a profile comprising a performance metric; monitor performance during the recommended workout; and when the performance does not match the performance metric, provide dynamic feedback based on the profile.

In one variant, the recommended workout is selected from a plurality of recommended workouts.

In one variant, the profile is matched for a user associated with the user apparatus.

In one variant, the dynamic feedback includes a revised workout. In one such variant, the user apparatus logs a revised performance with the revised workout.

In one variant, the dynamic feedback includes a motivational message.

Other features and advantages of the present disclosure will immediately be recognized by persons of ordinary skill in the art with reference to the attached drawings and detailed description of exemplary embodiments as given below.

BRIEF DESCRIPTION OF THE DRAWINGS

FIGS. 4A-4B are logical flow diagrams of methods for coaching a user based on workout history and/or personal fitness goals in a health tracking system, in accordance with the various principles described herein.

FIGS. 5A-5B are logical block diagrams of an exemplary server apparatus and health tracking devices useful in conjunction therewith, in accordance with the various principles described herein.

FIGS. 6A-6D are graphical representations of one exemplary user interface, consistent with the various principles described herein.

Figure 1:
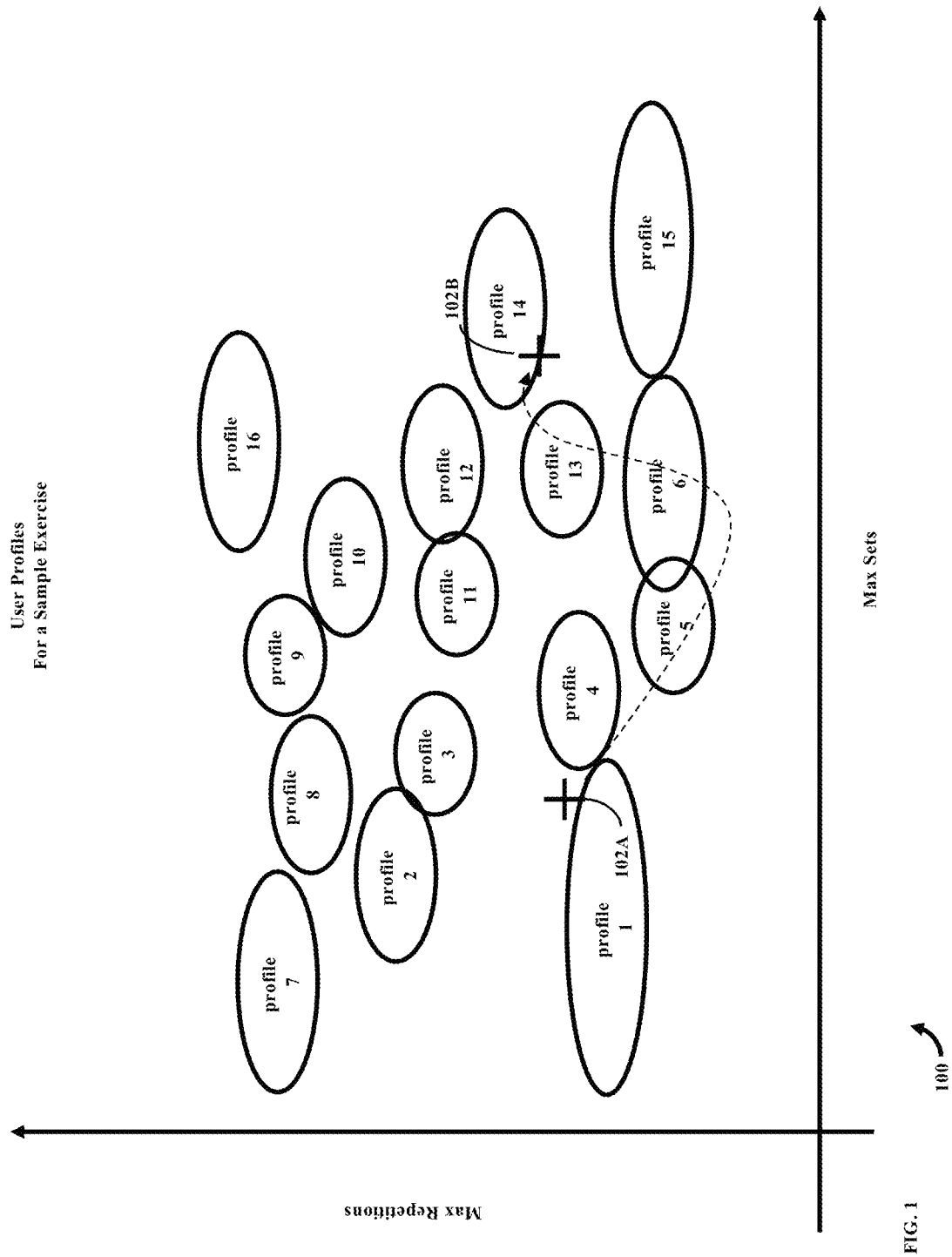
FIG. 1 is a graphical representation of user assessment, in accordance with the various principles described herein.

All Figures © Under Armour Inc. 2019. All rights reserved.

DETAILED DESCRIPTION

Disclosed embodiments include systems, apparatus, methods and storage media which enable workout recommendations and coaching based on workout history and/or personal fitness goals.

In the following detailed description, reference is made to the accompanying drawings which form a part hereof wherein like numerals designate like parts throughout, and in which is shown, by way of illustration, embodiments that may be practiced. It is to be understood that other embodiments may be utilized, and structural or logical changes may be made without departing from the scope of the present disclosure. Therefore, the following detailed description is not to be taken in a limiting sense, and the scope of embodiments is defined by the appended claims and their equivalents.

Aspects of the disclosure are disclosed in the accompanying description. Alternate embodiments of the present disclosure and their equivalents may be devised without departing from the spirit or scope of the present disclosure. It should be noted that any discussion herein regarding "one embodiment", "an embodiment", "an exemplary embodiment", and the like indicate that the embodiment described may include a particular feature, structure, or characteristic, and that such particular feature, structure, or characteristic may not necessarily be included in every embodiment. In addition, references to the foregoing do not necessarily comprise a reference to the same embodiment. Finally, irrespective of whether it is explicitly described, one of ordinary skill in the art would readily appreciate that each of the particular features, structures, or characteristics of the given embodiments may be utilized in connection or combination with those of any other embodiment discussed herein.

Various operations may be described as multiple discrete actions or operations in turn, in a manner that is most helpful in understanding the claimed subject matter. However, the order of description should not be construed as to imply that these operations are necessarily order dependent. In particular, these operations may not be performed in the order of presentation. Operations described may be performed in a different order than the described embodiment. Various additional operations may be performed and/or described operations may be omitted in additional embodiments.

For the purposes of the present disclosure, the phrase "A and/or B" means (A), (B), or (A and B). For the purposes of the present disclosure, the phrase "A, B, and/or C" means (A), (B), (C), (A and B), (A and C), (B and C), or (A, B and C). Similar logic applies to the use of the term "or" herein; i.e., "A or B" means (A), (B), or (A and B).

The terms "comprising," "including," "having," and the like, as used with respect to embodiments of the present disclosure, are synonymous.

Workout Routines and Human Physiology and Psychology

Most holistic health and fitness goals include some aspect of strength training and cardiovascular exercise. Similarly, many athletic activities (recreational, amateur, and/or professional) require significant strength and cardiovascular exertion. Thus, workout routines are generally categorized into cardiovascular workouts (e.g., walking, running, swimming, biking, etc.) and strength workouts (e.g., weightlifting, sprints, etc.) Some hybridized workout regimens mix both cardiovascular and strength training.

As a brief aside, the human body's cardiovascular system circulates oxygen and removes waste products from the skeletal muscles by pumping blood. The cardiovascular system relies on a unique type of cardiac muscle fiber to accomplish this task; cardiac muscle fiber is an involuntarily controlled muscle that is highly specialized and found nowhere else in the human body. The cardiovascular system's performance remains remarkably consistent over prolonged exertion.

In contrast to cardiac muscles, skeletal muscles are part of the human skeletal system (e.g., muscles, bones, tendons, ligaments, etc.) Skeletal muscles fatigue as a function of duration and intensity of use; their performance can be highly dynamic depending on composition. Modern research has shown that skeletal muscles are 3-dimensional structures of varying muscle fibers and connective tissue. Human muscle fibers are generally classified as "slow twitch" and "fast twitch", however muscle fiber types exist on a continuum and can express both slow and fast twitch qualities. The structure of skeletal muscles widely varies among different people; for example, some people may have muscle compositions that can easily provide bursts of activity at high load, others may have muscle compositions that provide sustained endurance at lower loads, etc.

Humans widely vary in their baseline physiology and psychology; these differences affect workout efficacy; for example, two people of different height, weight, fitness, musculature, and mental outlook may run 5 miles or lift weights with different levels of exertion and performance progression. As a practical matter, individual differences can introduce problems for people that exercise with a particular goal in mind.

For instance, most strength training routines are static and/or inflexible e.g., "20 kettle bell swings, 15 pounds", "15 bicep curls at 80% of maximum." Similarly, since the cardiovascular system is involuntary, cardiovascular workouts only indirectly exercise the muscles based on physical activity. Most endurance workouts prescribe a set time, set distance, etc. (e.g., "run 5 miles", "bike for 30 minutes.") Typically, these static workout routines assume a particular musculature and/or fitness level; there is no way to dynamically adjust the workout routine to suit individual needs. For example, a person that has suffered an injury may need to change a workout routine to prevent further injury. In another such example, a person may select a workout for 45 minutes during a lunch break but end up finishing too early (or take too long). In yet another example, a person may not be able to use required equipment (e.g., a specialized machine may be too busy during certain gym hours.) Even if the person has completed a modified workout, they may incorrectly log the workout data in their health and fitness tracking applications (e.g., over/under report activity, etc.)

As but another example, athletes often tailor their workout regime so as to improve performance for a particular athletic motion (e.g., throwing a ball, etc.) Many athletic activities incorporate multiple muscle groups working in concert (e.g., throwing a ball requires the arms, chest, back, stomach, and leg muscles to fluidly coordinate.) In contrast, most workout techniques and weightlifting equipment are focused on a single (or few) muscle group(s). While a professional athlete may be closely scrutinized by physical therapists and prescribed specific muscle group workouts to tune their performance, amateur and/or casual hobbyists seldom have access to the same resources. Instead they may resort to imperfectly copying workouts for lack of better alternatives. Unfortunately, this may result in widely diverging performance gains merely because they've over/under emphasized certain muscle groups.

As a related note, individual behaviors and motivations span a wide range. Some individuals are highly goal oriented in their workout regimen; other individuals may enjoy working out to "blow off steam." Some individuals may work through pain, even to their own detriment; others may need encouragement when a workout is difficult (but still doable). As a practical matter, these "intangible" factors are impossible to capture in static workout recommendations. Currently, dynamic feedback is only possible in the form of a human personal trainer/coach that actively observes an individual's workout; unfortunately, hiring a personal trainer can be cost-prohibitive for most gym goers.

Certain companies and/or gyms regularly publish workout routines via e.g., applications and websites, blogs, and other media sources, to boost gym attendance and/or attract new subscribers. While these services may provide well-intentioned information and/or generally acceptable guidance, there are no cost-effective solutions that are individually tailored. Furthermore, individuals with specific goals may be well aware of their own limitations and/or idiosyncrasies, and yet be unable to find workout routines that are germane to their personal fitness journey.

In view of the existing health and fitness ecosystem, improved solutions are needed to enable consumers to intelligently navigate their personal fitness journey. There exists a persistent need to provide efficient and easy-to-use mechanisms for getting relevant workout recommendations and coaching.

Example Operation

The exemplary solution described herein addresses the foregoing by providing workout routine coaching based on e.g., workout history and/or personal fitness goals. As previously alluded to, the wide variation in human physiology and psychology cannot be adequately addressed by static workout routines and workout progressions. However, an individual's performance can be predicted based on comparisons to groups of similar individuals. For example, power lifters have (or intend to develop) muscle performance similar to other power lifters. Likewise, endurance athletes have (or intend to develop) muscle performance similar to other endurance athletes. More directly, an individual's physiology and psychology can be modeled with an "expected profile" based on similar individuals; the expected profile can be used to recommend and/or provide dynamic feedback to users during their workout regimen.

In one exemplary aspect, the workout history for the population of users is analyzed to create one or more expected profiles. Each expected profile is associated with the heuristics and/or performance metrics for a subset of users having similar physiology and psychology. In one exemplary embodiment, the expected profiles are generated based on artificial intelligence (AI) and/or machine learning to identify similar users and their corresponding heuristics, rules, and/or patterns. While the exemplary embodiment is based on computer-assisted data science and data analysis techniques, other implementations may use human assessments (e.g., fitness experts, coaches, etc.) or some hybrid of human and machine learning. As described in greater detail infra, the initial expected profiles may be corrected and improved gradually over time as more and better crowd-sourced workout history is collected.

In one exemplary embodiment, a user may run through an initial assessment to grossly identify their "baseline" physiology and/or psychology. For example, establishing a baseline via an initial assessment may include one or more sets of squats, lunges, sit-ups, push-ups, pull-ups, abdominal rotations, a timed run, and/or a questionnaire (e.g., "how did you feel?", etc.) Completing the initial assessment provides baseline information as to the person's physiology (e.g., strength/stamina for each of the major muscle groups and/or cardiovascular endurance) and/or psychology (e.g., confidence, motivation, emotional state, etc.) In some cases, a user may be required to meet a minimum threshold of physiological and/or psychological performance for the assessment to be accurate. For example, a user that has never logged any workouts may be instructed to first establish a regular workout regimen before attempting assessment (e.g., "get in the habit of walking every day" before "run a timed mile.") Common metrics useful for generating a baseline or initial assessment may include, without limitation e.g., distance for an exercise (run, walk, bike, swim, etc.), repetitions accumulated, a particular pace threshold maintained for a specific duration, a minimum/maximum load, and/or any other physiological or psychometric metric.

Subsequently thereafter, the user may continuously update and/or augment input on their personal fitness goals and continue to track their workout history. Their baseline assessment, personal fitness goals, and/or ongoing workout history can be used to identify a matching expected profile. Subsequent workouts can be recommended to the user based on the matching expected profile. Similarly, during a workout, the user can receive dynamic feedback based on the expected profile; e.g., the user can be immediately notified and coached when they are over/under performing. In some cases, the user may be able to take corrective actions and/or accurately log their progress.

FIG. 1 is a graphical representation of user assessment (benchmarking), in accordance with the various principles described herein. As shown in FIG. 1, workout history is collected from a large population of users for an exercise (e.g., sit-ups, push-ups, squats, etc.) The workout histories are analyzed to generate a set of expected profiles. In this simple example, the expected profiles are shown in a two-dimensional "bubble chart" of maximum repetitions and maximum sets for an assessment exercise. More complicated embodiments may use a higher dimensional multi-variate analysis, the example of FIG. 1 being purely illustrative. Examples of variables that may be useful in a multi-variate analysis may include without limitation: age, sex, ethnicity, training load, training frequency, height, weight, and/or any number of other physiological and/or psychological parameters (e.g., behaviors, motivations, etc.).

Initially, the user benchmarks their performance in the assessment exercise. The user's performance is compared to the expected profiles; in this case, the user's performance 102A most closely matches expected profile: "profile 1". Profile 1 identifies the appropriate heuristics and/or performance metrics suitable for a subset of peers having similar e.g., physiology, psychology, and fitness goals. Notably however, as the user continues to regularly exercise and improve, their associated expected profile may change. For example, the user's performance metrics change over time (e.g., from performance 102A to performance 102B) and are associated with different expected profiles (e.g., profile 5, profile 6, . . . profile 14), these changes in expected profiles reflect the user's own personal fitness journey. Unlike conventional solutions that try to put every individual on a one-size-fits-all workout progression, the user's personal fitness journey changes the coaching and recommendations based on expected profiles that are most relevant to their current abilities and motivations.

Figure 2A:
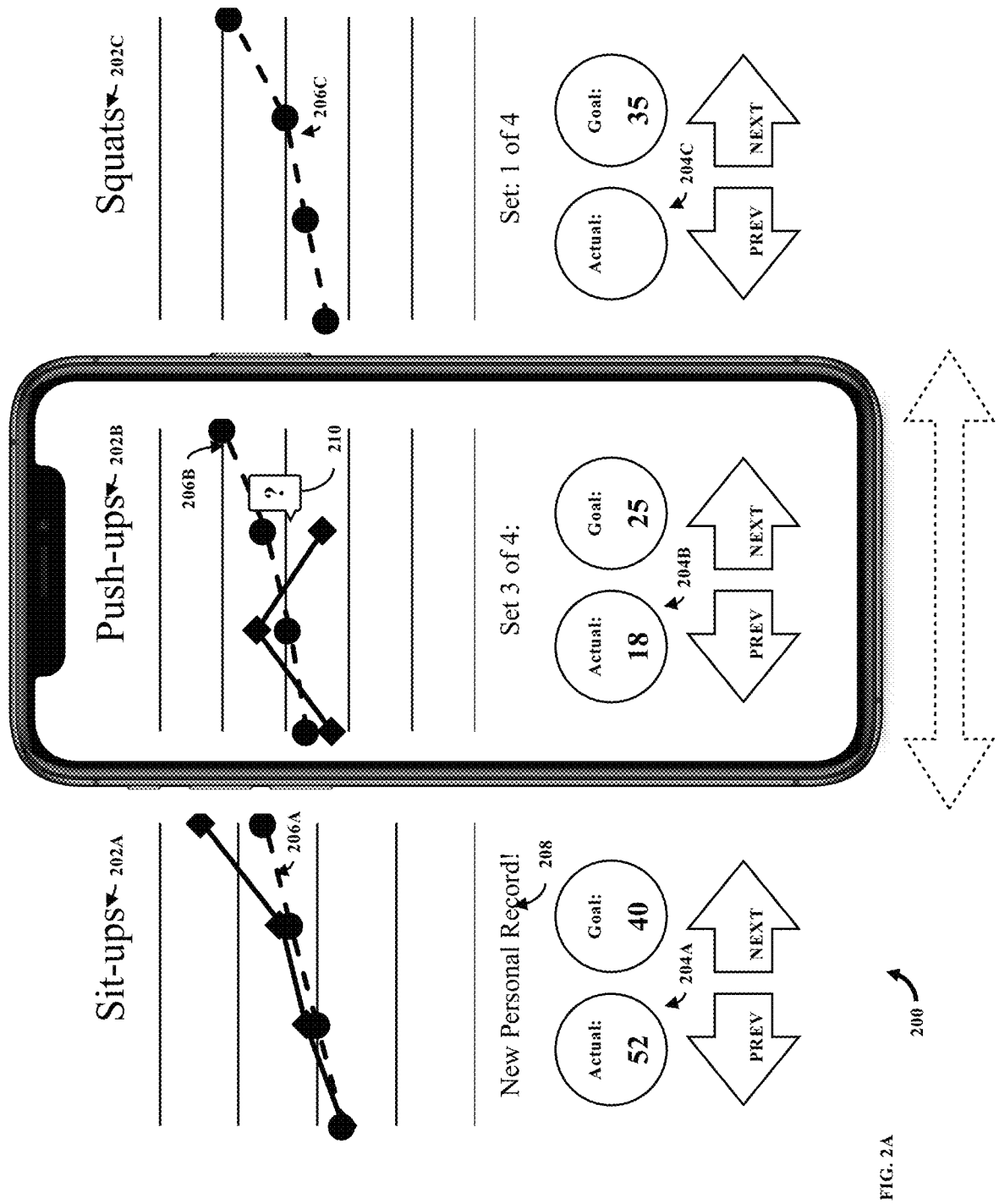
FIGS. 2A-2C are graphical representations of an exemplary workout coaching application, in accordance with the various principles described herein.

FIG. 2A illustrates one exemplary personalized workout recommendation and dynamic feedback user interface 200 based on workout history and/or personal fitness goals, consistent with the various principles described herein. As shown therein, the personalized workout recommendations are based on the heuristics and/or performance metrics associated with the expected profile. For example, the illustrated interface 200 recommends a set of exercises (e.g., "Sit-ups" 202A, "Push-ups" 202B, "Squats" 202C, etc.) and logs actual performance (204A, 204B, 204C) against an expected goal performance for the expected profile (206A, 206B, 206C). The user interface 200 may further include status e.g., a set count and/or motivational messaging ("New Personal Record!" 208).

A user may navigate the workout ("PREV", "NEXT") with virtual buttons. In the illustrated example, a user may also scroll through the workout using a horizontal user interface (UI) gesture (swipe back/forth) to select between activities. In some cases, the recommended workout may also provide the user with instructional information (e.g., exercised muscle group, proper form, why the exercise is important, etc.) In some embodiments, the interface 200 may be configurable based on user preferences. For example, a user may prefer vertical swiping in a "portrait" orientation (or change to a "landscape" orientation). Similarly, a user may prioritize, re-order, add, skip, start/stop timers, and/or remove workout recommendations. In some cases, a user may configure how workouts are displayed; for example, a user may prefer to see more or less detailed information e.g., bigger/smaller images, repetitions, weights, sets, distance, time, etc. Other variations of the interface 200 may be used with equal success.

Additionally, the exemplary user interface 200 can provide dynamic feedback 210 in response to such user input and/or during the workout. In some cases, dynamic feedback may be provided in response to skipping an exercise (e.g., "Why did you skip squats?"). In another example, as shown in FIG. 2A, a user that has failed to meet the expected performance may receive a notification (described in greater detail in FIGS. 2B-2C infra). Dynamic feedback may include a variety of different messages e.g.: interrogatory (e.g., "You have only completed 18 of 25 push-ups. How do you feel?), suggestions (e.g., "For this set, let's focus on form"), motivation (e.g., "You're doing great!"), information (e.g., "Push-ups in a wide stance or a narrow stance can activate different muscle groups"), status ("Only one more set to go"), etc.

While the illustrated embodiment uses visual feedback, other implementations may provide e.g., audible (voice, music, etc.) and/or haptic (vibration, etc.) feedback. Voice instruction, feedback, and/or commands may be useful where the user cannot directly touch the fitness tracking device. For example, during a push-up, the user's device may instruct the user to start a push-up with an audible "Down"; the user may respond with an audible "Up" to indicate the completion of a repetition. The user device may additionally provide feedback e.g., "That was too fast; for the next rep, slow down", etc. Similarly, haptic feedback may be useful for certain applications where the user can feel the device but need not directly respond (e.g., a smart watch may sense heart rate, and vibrate once a target heart rate has been reached, etc.)

Figure 2C:
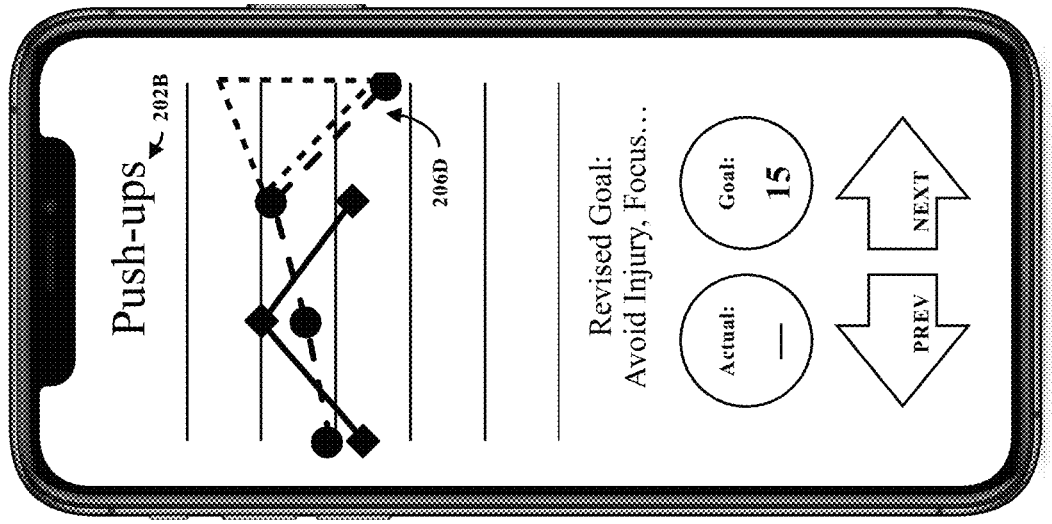
Figure 2B:
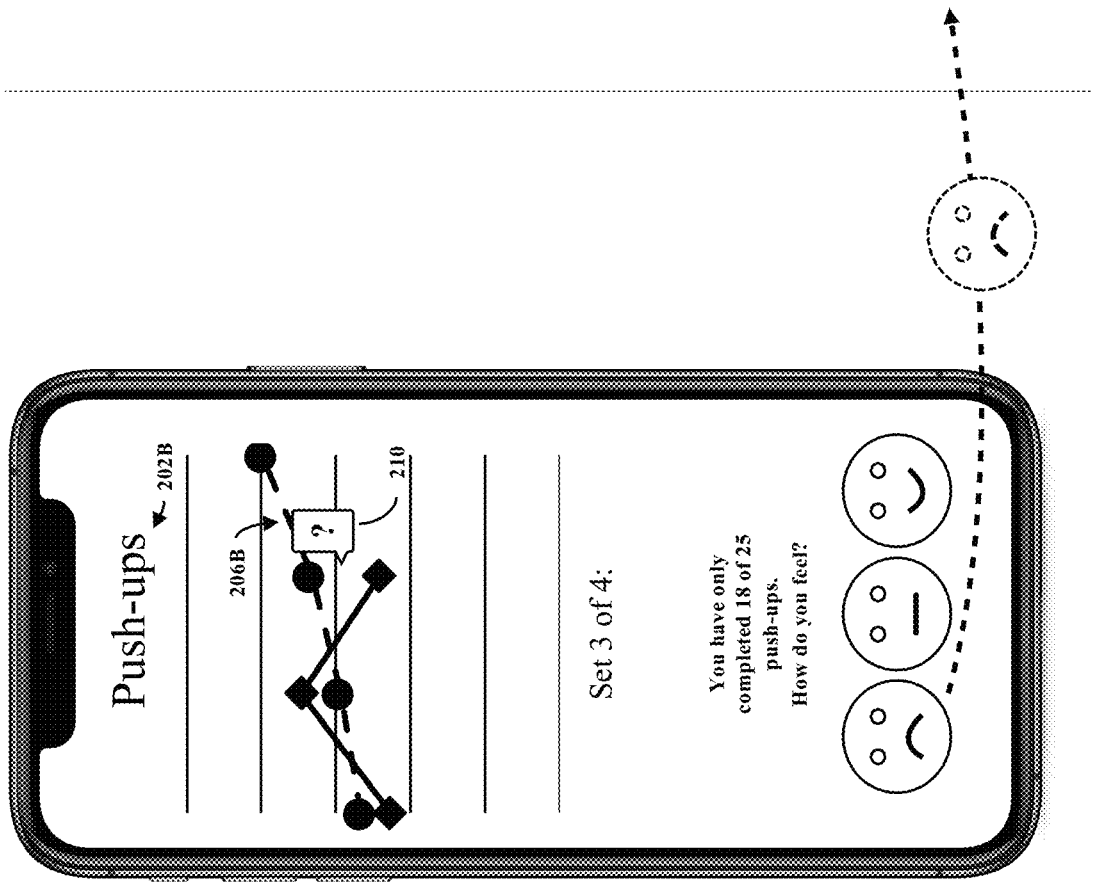

Referring now to FIG. 2B, one exemplary implementation of a dynamic feedback interface 250 is provided in greater detail. As shown therein, a user has failed to meet the expected performance. In the illustrated embodiment, the user device prompts the user to provide user input 210 to explain why. For example, a user may select a subjective emotional state (happy, indifferent, afraid of injury). In other cases, user input may be objective (e.g., injury, pain, inability, equipment unavailability, etc.) Still other types of user input may be provided, the foregoing being purely illustrative.

In response to user input, the user device adjusts the workout in accordance with the heuristics associated with the identified expected profile (revised interface 260 of FIG. 2C). In the example shown in FIG. 2C, the expected profile heuristics determine that the user's failure to meet expected performance is indicative of an increased risk of potential injury. Specifically, other users that are similar to this user and exercising under similar circumstances, are at increased risk of injury. Consequently, the workout is revised to an expected performance 206D such that the user can continue with a reduced goal; an informational note "Avoid Injury, Focus on Form" is also provided.

Notably, the heuristics for different expected profiles may vary widely; for example, a different heuristic could interpret the user's input as being indicative of lack of motivation. In response, the user device may offer more encouragement and/or suggest other more enjoyable activities. Still other heuristics may adjust subsequent workout stages so as to comply with a user's limitations; for example, a user that is taking longer than expected to finish the Push-up stage may be instructed to do a shorter run later on (so as to stay within a prescribed total workout time).

Once the user has completed the prescribed workout, the workout is logged appropriately (e.g., that the user revised the goal due to potential injury, and that the revised goal was met). In some cases, user input can be used to continuously improve the corresponding expected profiles and/or better match the user's performance with other expected profiles. In particular, users associated with an expected profile are treated similarly (e.g., prescribed similar workouts) because they are inferred to have similar physiologies and/or psychology. Performance progression for similar individuals results in positive feedback (further reinforcing the expected profile accuracy) whereas differences are negatively correlated (pushing users toward better fitting expected profiles). In other words, improvement to the user's classification and the expected profiles may be an emergent property of continuous user workout history analysis.

More generally, the disclosed embodiments of the present disclosure ensure that users receive instantaneous, accurate, and targeted feedback which can greatly improve the progression of workout performance. The disclosed solutions enable users to conveniently navigate their personal fitness journey. The foregoing discussion of the exemplary implementation is purely illustrative; artisans of ordinary skill in the related arts may add, remove, and/or substitute similar functionality, given the contents of the present disclosure.

Network Architecture

Figure 3:
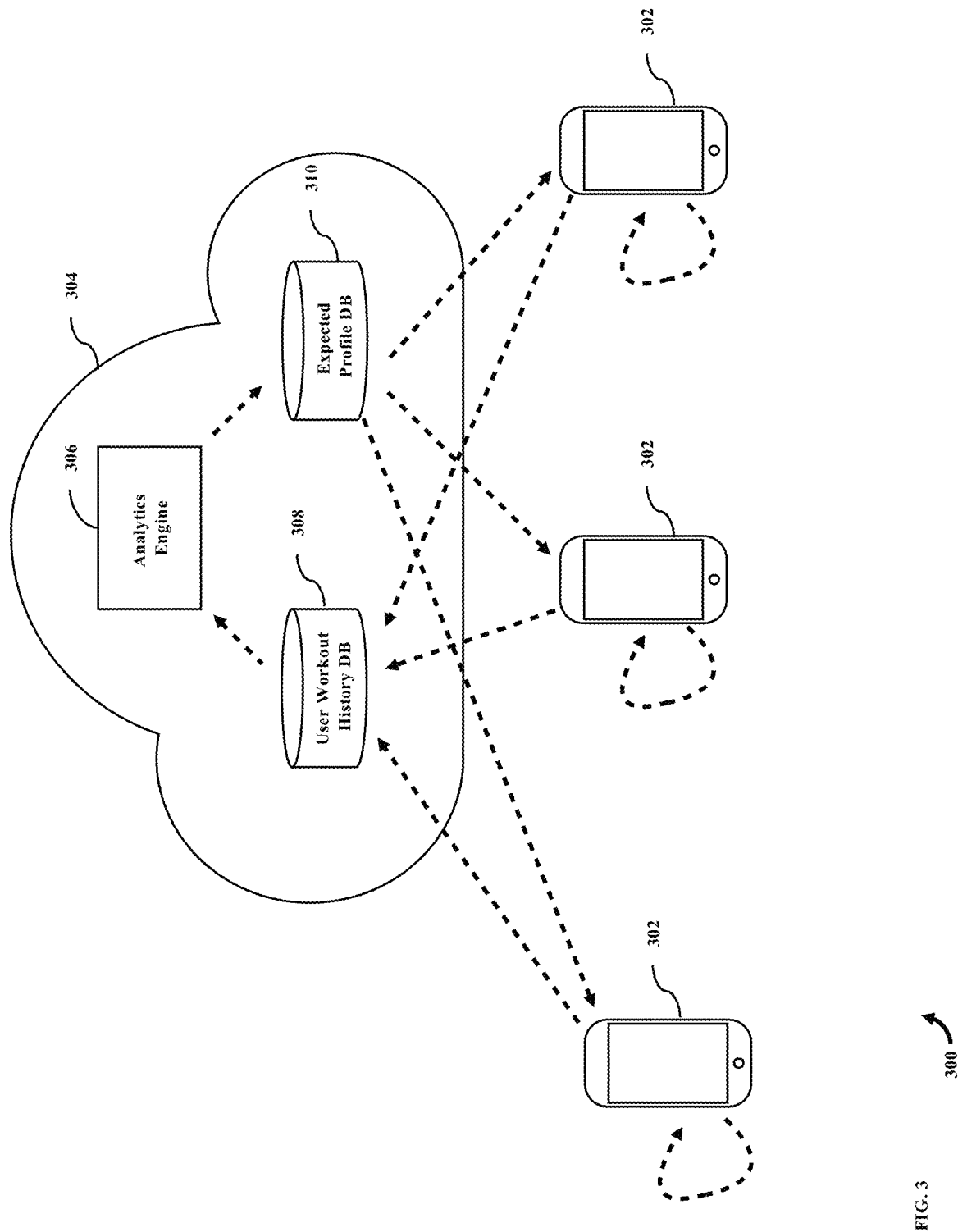
FIG. 3 is a logical block diagram of an exemplary network architecture configured to enable workout coaching based on workout history and/or personal fitness goals, in accordance with the various principles described herein.

Referring now to FIG. 3, an exemplary network architecture 300 configured to enable workout coaching based on workout history is shown. As illustrated, the system 300 includes one or more user devices 302 in communication with a health tracking network 304. In one exemplary embodiment, the health tracking network 304 may include one or more of an analytics engine 306 in communication with a user workout history database 308 and a database of expected profiles 310.

The health tracking network 304 may include one or more wired and/or wireless, private and/or public network, including but not limited to, e.g., the Internet. The health tracking network 304 is, for example, a wireless local area network (WLAN), wireless wide area network (WWAN), wired network, or any other suitable communication channel. Accordingly, each of the user devices 302, analytics engine 306, and databases (e.g., user workout history database 308 and expected profiles database 310) are configured with appropriate networking communication interfaces. An example of wired communication interface may include, but is not limited to, Ethernet; while examples of wireless communication interfaces may include, but are not limited to, near field communication (NFC), Bluetooth, WiFi, 4G or 5G LTE. It is further appreciated that various gateways, routers, switches, base stations, and so forth may be involved in facilitating and forwarding communication between the foregoing devices. Additionally, it is noted that the foregoing health tracking network 304 may be itself, composed of several networks, such that the described components are distributed in various ones thereof. In alternative embodiments, the health tracking network 304 may include a series of devices communicating within software via software API's.

As used herein, the term "database" refers to a structured set of data records held within a non-transitory computer-readable medium and/or the mechanisms used to e.g., add, remove, modify, and/or query and retrieve the stored data records. The term "data record" refers to a collection of data structures that represent an association, grouping, organization, or other collection of information; common examples of data structures include without limitation: numbers (integers, floating point), values (Booleans, enumerations), characters, strings, arrays (1D, 2D, N×D, etc.), lists, hash tables, etc. For example, a database may be queried for one or more data records that satisfy a particular condition; e.g., containing a particular string, value, etc.

The user workout history database 308 stores a plurality of user data records and their corresponding workout data records. Each user data record may include detailed information with regard to e.g., accuracy of data, fitness goal definition, progression of performance, psychological parameters (e.g., behaviors, motivations, etc.), height, weight, age, sex, ethnicity, and/or any number of other user specific parameters. Each workout data record may include detailed information with regard to e.g., date/time of past exercises, scheduled date/time of future exercises, type and/or number of exercises, frequency of exercise, exerted muscle groups, duration of exertion, intensity of exertion, absolute load, relative load, range of movement, repetition, recovery time, fatigue, dynamic feedback/user response, frequency of revision, revision success/failure, and/or any number of other workout specific parameters. More generally, artisans of ordinary skill in the related arts given the contents of the present disclosure, will readily appreciate that virtually any data regarding either the individual users and/or their specific workout history can be stored.

The expected profiles database 310 stores heuristics and/or performance metrics for one or more expected profiles. For example, an expected profile may define a muscle group (e.g., abdominals), an associated exercise (e.g., sit-ups), and a workout with a series of expected performances and acceptable ranges (e.g., four (4) sets of increasing repetitions (25, 30, 35, 40) plus or minus 1 set, 5 sit-ups). Users that are associated with the expected profile should be able to meet the expected performances. Actual performance that deviates from the expected performance beyond an acceptable range may trigger execution of a heuristic and/or feedback. For example, a user that exceeds their expected performance range (e.g., performing 50 sit-ups where only 35-45 sit-ups were expected) may receive congratulatory feedback, a user that underperforms the expected performance range may be encouraged to improve and/or cause modification to subsequent workouts. In some cases, the heuristics may take user input into account, for example, a user that reports positively (e.g., "I've almost got it, let me try again") may have a smaller correction than a user that subjectively reports negatively (e.g., "I think that's all I got").

It is appreciated that in the illustrated embodiment, the aforementioned databases (308, 310) are separate and distinct from the analytics engine 306 and/or user device(s) 302. However, in other variants, the databases may be incorporated in part or in whole with either the analytics engine 306 and/or the user device(s) 302 for storage thereat. For example, workout data records that have been logged (or scheduled) at a particular user device 302 may be stored locally until e.g., synchronized with the network (or vice versa). Additionally, or in the alternative, expected profiles (in whole or in part) may be stored at the analytics engine 306 and portions may be made accessible to particular devices 302 when queried and/or locally cached. Any combination of the foregoing configurations may be utilized with equal success.

While the foregoing example is presented in the context of strength training/calisthenic/cardiovascular type routines, artisans of ordinary skill in the related arts will readily appreciate that the various principles described herein may be readily adapted to virtually any physical activity e.g., sports activities, etc.

Methods

FIG. 4A is a logical flow diagram of an exemplary method 400 for providing workout routines to a user based on workout history, in accordance with the various principles described herein.

At step 402 of the method 400, a health tracking system analyzes workout data to generate one or more profiles. In one embodiment, workout data for a large population of users is analyzed to classify users into "groups" that are physiologically and/or psychologically similar. In one exemplary embodiment, the identified "group" is analyzed to create an expected profile that parameterizes heuristics and/or performance metrics for its constituent members.

In another embodiment, workout data for specific individuals is analyzed to identify physiological and/or psychological traits for that individual. For example, celebrities and/or athletes may have their own workout data analyzed. The celebrity and/or athlete may then publish their workout data such that other individuals can aspire to holistically steer their workouts to match the celebrity/athlete. More directly, even though a professional athlete may focus on strength training for specific muscle groups, an amateur may actually need to improve many different muscle groups to achieve similar results. In other words, the celebrity profile can be used to dynamically coach a person toward an aspirational level of fitness of another person.

In still another embodiment, workout data for a specific group of individuals may be analyzed. For example, an athlete may want to tailor their workouts to match against a peer set of specific athletes, e.g., a running back for a football team may want to know how they compare against all running backs in the league. Still other variants of the foregoing may be substituted with equal success, by artisans of ordinary skill in the related arts.

Referring back to step 402, the workout data analysis can be performed via machine learning and/or other artificial intelligence (AI) techniques. Specifically, machine learning and/or artificial intelligence (AI) can be used to filter populations of users into subsets having similar characteristics. Each subset is associated with appropriate performance metrics based on e.g., workout history, interpolation/extrapolation from workout data, interpolation/extrapolation based on related muscle group exercises and workouts (e.g., pull-ups may enable some extrapolation to similar muscle exercises e.g., bicep curls, etc.) and/or user input/responses. In other implementations, performance metrics can be assigned based on expert human analysis or even explicit user responses/input (e.g., similar circumstances where users report similarly, etc.).

In one embodiment, the analysis generates one or more profiles. In one exemplary embodiment, profiles can be continuously updated based on crowd-sourced data from actual users. In other embodiments, the profiles may be generated initially, but subsequent data analysis and profile updates are triggered based on threshold events (e.g., based on excessive deviation, etc.) Still other techniques may perform analysis on a periodic basis, aperiodic basis, etc.

In one exemplary embodiment, the analysis may be subdivided into "stages" of analysis; for example, the analysis may need to identify which subsets of user workout data should be grouped together and/or what patterns and relationships exist in the subsets of user workout data. In another example, analysis may be iterative over time. For example, as user adoption increases and workout data continues to accumulate, data analysis may be repeated so as to continuously improve the accuracy and/or robustness of the profiles.

As used herein, the terms "analyze" and "analysis" refers to any technique, method, process, algorithm, and/or system that examines a data set to extract relationships from the data set. Analysis may be manual (e.g., entry based on human analysis), automatic (machine learning), or a hybrid thereof (e.g., software identification with human acknowledgement, etc.) More generally, artisans of ordinary skill in the related arts given the contents of the present disclosure, will readily appreciate that virtually any scheme for data analysis may be substituted with equal success the following being purely illustrative.

As a brief aside, humans are good at interpolating and/or extrapolating relationships in relatively small amounts of data. Traditional examples of such relationships include, without limitation: predictive relationships, causative relationships, correlative relationships, statistical behavior, probabilistic behavior, and/or any arithmetically defined function. However, human analysts are expensive to employ and are poorly suited for analyzing large, "noisy", multi-variate data sets. Additionally, certain types of data analysis are "mining expeditions" that are commercially infeasible to pursue with human labor e.g., the result may be too low yield, unpredictable, sparse, etc. Recently, however, advances in data science and machine learning have enabled automated identification and recognition of patterns in data sets. Computer-based data analysis greatly expands the breadth and/or depth of relationships that can be identified in large data sets.

Machine learning algorithms vary widely in their approach, data requirements, and tasks/capabilities. Machine learning typically involves creating a model, which is trained to process data to make predictions therefrom. Common examples of machine learning models include e.g., artificial neural networks, decision trees, support vector machines, Bayesian networks, genetic algorithms, and hybrids thereof. Common techniques for training include supervised learning, unsupervised learning, reinforcement learning, feature learning, sparse dictionary learning, anomaly detection, multi-variate association, etc.

In one embodiment, different types of data may be analyzed with different types of machine learning. For example, user classification may be based on supervised learning, whereas heuristic and performance metric generation may be based on unsupervised learning. As a brief aside, supervised machine learning uses training data to infer relationships where the input and output data types are known. Supervised learning models may be particularly suitable for e.g., identifying which users should be grouped together under an expected profile because training data can include clear examples of endurance athletes, sprint athletes, etc. In contrast, unsupervised machine learning can be used to identify patterns in unstructured data (e.g., where there is no clear definition of "input" or "output"). In other words, once the users for an expected profile have been identified, unsupervised learning may be used to "mine" for unknown characteristics about the users to generate heuristics and performance metrics for the expected profile.

There may be a myriad of situations that require further derivation, inference, exploration, and/or feedback because the machine learned relationships are ambiguous or inaccurate. In such cases, it may not be possible to classify the data with machine learning, without further human assistance (e.g., user input, expert analysis, etc.) For example, a user may need to provide additional feedback via explicit input, a fitness test, sport evaluation, or otherwise provide proxy data (data representative of an immeasurable quality) useful to support more accurate user profiling. In other cases, a physician or sports expert may be able to identify intangible factors that lay outside of the collected data.

In another such example, user classification can be continuously improved based on new information using reinforcement learning. More directly, once a user has been associated with an expected profile, the resulting actual workouts logged by the user can be used to further reinforce (or weaken) the strength of both the user's match and/or the expected profile. In other words, the classification of a user should change as the user's personal fitness journey changes. User progression obviously benefits the user but may also be used to further tune the health tracking systems classification, coaching, and/or recommendation accuracy.

Still other techniques for data analysis using machine learning may be added, modified, substituted, parallelized, and/or sequentially cascaded, by those of ordinary skill in the related arts, given the contents of the present disclosure.

Referring back to step 402, various embodiments analyze workout data to extract relevant patterns in physiological and/or psychological data. Common examples of workout data may include, without limitation: fitness goal definition, progression of performance, muscle group, duration of exertion, intensity of exertion, absolute load, relative load, range of movement, repetition, recovery time, psychological parameters (e.g., behaviors, motivations, etc.), height, weight, age, sex, ethnicity, and/or any number of other user specific workout parameters.

More generally, however, any parameter that affects user performance may be considered. For instance, environmental conditions may affect human physiology and/or psychology. Such environmental factors may include e.g., elevation, temperature, humidity, sound (music), other people (workout buddies), season, and/or any number of other considerations. As but one example, a user that lives at sea level may perform differently (and thus require different coaching) when they are at a different elevation.

Due to the sensitive nature of user data, various embodiments of the present disclosure may additionally anonymize certain information. In one exemplary embodiment, the user may select what information may be analyzed. In some variants, the user may be able to protect personally identifying information (name, height, weight, age, sex, etc.) In some variants the user may be able to protect workout related information (e.g., time, location, duration, frequency of workout, etc.) As but one example of anonymization, identifying information may be unidirectionally hashed, scrambled, encrypted, and/or otherwise obscured.

In alternative embodiments, user identifying information may be used e.g., to improve accuracy. For example, a first set of profiles may be generated from anonymized user workout data for users that do not want to release sensitive information and a second profile may be generated from private user workout data for users that waive their privacy. The second profile may offer additional benefits and/or better coaching based on the improved specificity. For example, location and/or demographics (age, ethnicity, sex) information may provide better psychographic profiling useful for niche motivational messaging.

In order to prevent malicious activity (e.g., polluting performance metrics with misreporting, etc.), the user may be required to verify their authenticity in order to e.g., create user accounts and/or generate workout data. For instance, the user may be required to provide proof of existence (via e.g., an external email account, phone number, or other personal verification method). Additionally, in some cases, a user account may be validated to ensure that the user profile information is reasonable. For example, age, height and/or weight inputs may be verified to lie within the realm of possibility. In some cases, external verification of personhood may require certification (trust credentials) or other root of trust (e.g., trusted 3rd party verification, etc.) Still other techniques for managing user database integrity may be substituted with equal success by artisans of ordinary skill in the related arts.

As used herein, the term "workout" refers to one or more activities performed by the user with measurable physiological and/or psychological impact. Examples of measurable physiological impacts may include without limitation e.g., cardiovascular strain, heart rate, caloric consumption, muscular exertion, fatigue, blood oxygenation, lactate production, blood occlusion, nervous system activation, temperature increase, sweat production, changes to form/body positioning (via video analysis), audible data (exhalations, foot strikes, etc.), and/or any other physical effect of exertion. Physiological data may be collected via one or more sensors and/or the user device interface (e.g., buttons, touch screen, microphones, etc.). Common examples of sensors include e.g., accelerometers, heart rate monitors, blood sensors, microphones, cameras, etc.

As used herein, "performance" and "performance metrics" refer to any set of workouts and/or predicted/expected physiological and/or psychological impacts for similar users based on e.g., physiology, psychology, fitness goals and/or any other relevant parameters. As used herein, the term "performance progression" is used to refer to a user's tolerable physiological and/or psychological impact as a function of time. For example, a user's physiological progression may be measured as a function of e.g., changes to heart rate as a function of distance run over multiple workouts, changes to maximum repetitions/sets of a load over multiple workouts, etc. Notably, while performance progression is generally measured physiologically, psychological measures may also have significant value. For example, some users may subjectively enjoy working out regardless of whether or not they improve their physiological performance. Also, a user's psychological impact may cause changes to motivation and/or outlook when they hit a physiological "plateau."

In one exemplary embodiment, heuristics refers to any logic that is configured to dynamically respond to user input. In one exemplary embodiment, the heuristics are conditional rules for execution by a processor of the user device. As used herein, the term "conditional" refers to any action or event that is subject to one or more logical conditions or requirements being met. Common examples of conditional rules include e.g., "if-then", "only-if-then", "do-until", "perform-while-true", "case(s)", and/or other Boolean logic. While the conditional logic is described herein, artisans of ordinary skill in the related arts given the contents of the present disclosure will readily appreciate that non-Boolean based rules may be substituted for conditional rules with equal success. Common examples of non-Boolean rules include without limitation: machine learned rules, pattern-based rules, predictive rules, weighted rules, "fuzzy" logic, and/or other techniques.

At step 404 of the method 400, the health tracking system recommends workouts to clients based on the expected profiles. In one embodiment, workout recommendations may be based on the expected profile and one or more of e.g., user data records, workout data records, environmental factors, advertising, or other health tracking system processes. In one exemplary embodiment, the expected profiles may be associated with heuristics and/or performance metrics that enable the client device to identify salient events and/or provide dynamic feedback in view of the recommended workout. Each recommended workout may identify one or more exercises, the expected performance corresponding thereto, and/or the conditions under which the user has deviated from expected performance.

For example, a client device may receive a workout that prescribes a set of exercises, an expected number of sets/repetitions, and/or rules for adjusting the workout if the user is underperforming due to injury or lack of motivation. In other embodiments, the health tracking system may push a number of workouts to a client device that are generally associated with the user's closest matching expected profile. When the user wants to do a workout (or schedule a workout for later), they can select one of the pushed workouts.

In another exemplary embodiment, a set of workouts may be "pulled" by a client device based on e.g., user parameters, the user's profile, previous workout history, or other client-side considerations. For example, a user may walk into their gym and identify equipment that is available (e.g., treadmills, kettlebells, and seated row) and/or their total time for working out (e.g., 45 minutes), responsively the health tracking system can identify workouts for the expected profile that best match the user's specified criteria. In another such case, a set of workouts may be pulled based on user input; for example, a user that has injured themselves (or cannot complete an assigned workout) may pull alternative workouts for their expected profile. Similarly, a user that has to adjust their workout intensity may need to get different workout routines mid-workout for their expected profile.

In some cases, a super set of workout suggestions may be pushed to a user and cached for internal retrieval. In one example, a user may generally receive a suggested set of routines that should be completed within e.g., a week. Any of the workouts can be locally queried, scheduled for activity, and/or logged at the client device without requiring further health tracking system interaction. In another example, a user may be "cusping" from one expected profile to another. The health tracking system may push suggested workouts that are associated with both profiles. Thereafter, the client device may be able to dynamically bridge between the suggested exercises during the user's workouts, thereby smoothly transitioning the user throughout their personal fitness journey.

In some situations, a hybrid of "push" and "pull" may be used. For example, a user may pull a first set of workouts, and be pushed a second set of workouts based on the expected profile; e.g., a user may request upper body workouts, which additionally cause lower body workouts to be delivered in tandem. In other cases, a user that requests a workout may be suggested with alternative workouts so as to vary a user's workout schedule. For example, a user that has explicitly selected a "20-minute walk" may be pushed other workouts having similar effect (e.g., "mild calisthenics").

While the foregoing example is presented in the context of a health tracking system and client device interaction, artisans of ordinary skill in the related arts will readily appreciate that workouts may be provided via alternative sources and/or avenues. For example, a client device may send/receive workouts to/from other client devices and/or other parties; e.g., a smartphone that is paired to a smartwatch can provide workouts thereto. Similarly, a user may be able to send recommended workouts to a training partner, etc. In some cases, user transfers may occur in a broadcast or multicast manner; for example, a coach may send a team of athletes a set of workouts. Each athlete may have their own set of workouts further personalized based on their specific needs.

At step 406 of the method 400, the health tracking system updates the workout data with logged workout performance. As used herein, "log" and/or "logging" refers to any addition, derivation, inference, and/or subsequent manipulation of data records directed to user activity. Logging may be manual (e.g., entry by a user, personal trainer, coach, and/or other human), automatic (machine entry via e.g., client device, health tracking server, $3^{rd}$ party service, etc.), or a hybrid thereof (e.g., machine logged with human acknowledgement, etc.) More generally, artisans of ordinary skill in the related arts given the contents of the present disclosure, will readily appreciate that virtually any scheme for logging may be substituted with equal success, the following being purely illustrative.

In one embodiment, a workout data record is received from the client device and associated with the user profile. In one exemplary embodiment, the workout data record includes e.g., time and/or date of workout, detailed information with regard to e.g., type and/or number of exercises, exerted muscle groups, duration of exertion, intensity of exertion, subjective user input, and/or any other workout specific data. Additionally, the user data record may include any salient events e.g., where a heuristic was triggered and/or performance metric was exceeded/not met by a prescribed range. Salient events and/or dynamic feedback may include e.g., substitute exercises, added/removed exercises, completion status, duration, physiological and/or psychological impact and/or other user input. For example, a user may additionally add personal notes and/or user tags (e.g., "Personal Best", "Strained hamstring on $3^{rd}$ set", etc.)

Dynamic feedback for users may be an important source of information for updating expected profiles. Empirical evidence suggests that while user subjectivity varies between individuals, it is generally consistent over time for the same individual (e.g., a user that underreports discomfort is likely to consistently underreport, etc.) Consequently, various exemplary embodiments of the present disclosure may use subjective data (user input) to further improve the heuristics and performance metrics associated with expected profiles. In some cases, subjective reporting may be difficult for non-human interpretation. Thus, some variants may provide anonymized user input to a human (e.g., a physical therapist, etc.) for interpretation, validation, verification, and/or translation into objective metrics for updating expected profiles.

In other embodiments, dynamic feedback to workouts may be specific to a user. For instance, the user may be able to "opt out" of providing subjective input, and their workout data records may be excluded from expected profile updates. Non-disclosed user input may detract from the accuracy and/or quality of a user's feedback. Validation and/or verification of non-disclosed user input may be unnecessary. Similarly, some variants may additionally allow for post-workout logging. In some cases, the post-workout logging may be manual and/or user specific; in other cases, the post-workout logging may be automatic based on conditional rules.

In some embodiments, the user profile may be updated based on analysis of the user's workout data records. For example, a user that consistently falls below their personal health and fitness goals may receive encouragement and/or feedback to re-evaluate their goals. In some cases, user workout data records may be matched against expected goals to ensure that adequate progress is being made. Logging is prone to error and/or misreporting; e.g., some users may consistently under/overreport their workout regimen. Analyzing a user's own performance against the expected performance metrics of an expected profile may assist in user expectations and/or correct for misreported data. For example, a person that is consistently overreporting their workouts may show subpar performance gains. Under such situations, the health tracking system may further adjust the user's profile consistent with a different expected profile and/or remind the user that tracking efficacy is based on diligent record keeping.

FIG. 4B is a logical flow diagram of an exemplary method 450 for coaching a user with dynamic feedback, in accordance with the various principles described herein.

At step 452 of the method 450, a client device receives workout recommendations from a health tracking system and prompts the user to select a workout. In some cases, the client device may directly provide the workout recommendations to the user. In other cases, the client device may consider other client-side considerations to further winnow down recommended workouts. For example, a user may locally impose restrictions (e.g., no workouts longer than 45 minutes, ignore workouts when outside of a geo-fenced "home gym" area, ignore workouts during injury/recovery periods, etc.)

In one embodiment, the workout recommendations may be received from a health tracking system based on the user's profile and/or one or more closely matching expected profiles. In other embodiments, the workout recommendations may be further filtered by the client device based on client-side information (e.g., user schedule, available equipment, user mood, etc.) e.g., to focus on the subset of workouts that the user is interested in. Still other embodiments may hybridize client-side and server-side considerations. For example, the user may frequently pick their own workouts, while still being open to workouts recommended based on expected profiles.

Once a workout is recommended and selected, the client device monitors performance during the selected workout and provides dynamic feedback (if necessary) at steps 454 and 456 of the method 450. In one embodiment, the user may input workout data into the client device and receive dynamic feedback via a visual user interface. In one such variant, the user interface may be a natively executed application running on a user's device (e.g., smart phone, watch, laptop, etc.). Other common embodiments may use a web browser, or other intermediary web portal located at home or at a gym. Users may use a screen, keyboard, and mouse or other computer peripherals to interact with the displayed workout (e.g., to see the various exercises, input repetitions/sets, etc.)

In other embodiments, the user may provide auditory input to the client device and receive dynamic audible feedback therefrom; e.g., the client device may read workout instructions aloud and/or accept voice commands. For example, the client device may instruct the user to start a push-up with an audible "Down"; the user may respond with an audible "Up" to indicate the completion of a repetition. In a similar embodiment, haptic type interfaces may use accelerometers and/or haptic feedback to communicate with the user. For example, the client device may vibrate to instruct the user to start a repetition, the user's motion (captured via accelerometer) may indicate completion of a repetition. Still other types of user interface may be substituted by artisans of ordinary skill in the related arts, given the contents of the present disclosure.

In one embodiment, the client device monitors for salient events and/or conditions where a heuristic was triggered. For example, the heuristic can specify an expected performance metric within a prescribed range. Other common examples of heuristics may include without limitation e.g., completion of an exercise too quickly/slowly, heart rate being to high/low, irregularity of form, excessive/minimal strain (via blood occlusion, oxygenation, lactate, etc.), and/or any number of other indicia.

As but one example, the heuristic may specify a number of repetitions; the client device counts repetitions, if the user cannot meet (or exceeds) the specified number of repetitions, then the client device provides dynamic feedback and/or modification to the recommended workout (e.g., by increasing or reducing the next set's repetitions). In another such example, the heuristic may specify an expected time of completion (e.g., each repetition/set should be completed within a time window), failure to remain within the time window may be indicative of fatigue or incorrect form. Still other examples may monitor a user's psychological state; for example, a user that is tired early may be allowed to cut their workout short to prevent injury, or urged to complete the entire workout, depending on the expected profile's psychometric rules.

In some embodiments, the user may enable, disable, and/or postpone dynamic feedback. For example, some users may find dynamic coaching distracting during an exercise, but may be interested in receiving feedback later (e.g., during a rest period, etc.) In these circumstances, the client device may track status, but only provide feedback when the user expressly wants to know how they did. In another such example, some users may not want dynamic feedback in the form of coaching but are open to changes to the workout routine. In some such variants, the user may be able to see when and why the workout changed (if interested).

In still other embodiments, a user may be able to provide their user to another user. For example, a user may want to provide their dynamic feedback to a personal trainer. In this manner, the user may benefit from personal trainer advice without paying the personal trainer to watch them exercise. Similarly, the personal trainer may be able to remotely coach a much larger clientele.

Various other schemes for monitoring a user's progress in view of an expected profile will be readily appreciated by artisans of ordinary skill, given the contents of the present disclosure.

At step 458 of the method 450, the client device logs the user's actual workout data. In some embodiments, the user may be prompted to reconcile monitored exercise with the actual exercise performed. For example, a user may have been recommended an exercise, but decided to do something else (due to injury, equipment availability, mood, etc.) In other examples, the client device's sensors may be unable to accurately gauge completion, inaccurate, and/or faulty. The actual workout data records should only reflect what the user completed (or failed to complete). Actual user workout data may be stored as user workout data records, which may be stored at either or both of the client device and/or the health tracking system.

In some embodiments, a user may be able to locally access their user workout data records. In some cases, the user's immediate access to previous user workout data records may be useful to e.g., track progress, plan for future workouts, and/or used for other motivational purposes. In some cases, the user workout data records can be made accessible via e.g., external application programming interfaces (APIs) to a variety of other tools.

More generally, artisans of ordinary skill in the related arts will readily appreciate that a wide expanse of usability may be necessary with individualized user workouts. In an ideal world, every workout can be perfectly logged, yet real world considerations exist. While accuracy is important, "perfect" adherence is not required for user benefit; "good enough" may suffice to keep users on their personal health and fitness journey.

While the foregoing examples are presented in the context of a single workout, artisans of ordinary skill in the related arts, given the contents of the present disclosure, will readily appreciate that a workout regimen can be steered over time so as to enable a user to achieve particular fitness goals. As but one example, a casual athlete user (e.g., classified in a first expected profile) might have a goal to improve their sport performance in view of a sports idol (e.g., a second expected profile.) The most realistic way for the casual athlete user to achieve their goals may be greatly affected by their physiological and psychological characteristics. In some cases, similarly situated and motivated users may have greater success by e.g., focusing on physiological goals (e.g., working on one muscle group before another, focusing on flexibility, etc.) and/or psychological goals (e.g., establishing a regular workout discipline, pushing through discomfort, etc.) In other words, steering users to improve and transition to new expected profiles may be more efficient to achieve performance progression than others.

Apparatus

FIG. 5A is a logical block diagram of one exemplary server apparatus 500, useful in accordance with the various principles described herein. In one embodiment, the server apparatus 500 includes a processor 502, non-transitory computer-readable medium 504, and one or more network interfaces (e.g., a first network interface 506, and a second network interface 508).

The components of the exemplary server apparatus 500 are typically provided in a housing, cabinet or the like that is configured in a typical manner for a server or related computing device. It is appreciated that the embodiment of the server 500 shown in FIG. 5A is only one exemplary embodiment of a server 500 for the health tracking system. As such, the exemplary embodiment of the server 500 described herein with reference to FIG. 5A is merely representative of any of various manners or configurations of servers or other data processing systems that are operative in the manner set forth herein.

The processing circuitry/logic 502 of the server 500 is operative, configured, and/or adapted to operate the server 500 including the features, functionality, characteristics and/or the like as described herein. To this end, the processing circuit 502 is operably connected to all of the elements of the server 500 described below.

The processing circuitry/logic 502 of the host server is typically controlled by the program instructions contained within the memory 504. The program instructions 504 include a workout coaching application that enables dynamic feedback as explained in further detail supra. The workout coaching application at the server 500 is configured to communicate with and exchange data with the client-side workout coaching application running on a processor of the health tracking devices. In addition to storing the instructions 504, the memory 504 may also store data for use by the health tracking program. As previously described, the data may include the user data records, the user workout data records, and/or expected profiles.

The network interfaces of the server 500 allows for communication with any of various devices using various means. In one particular embodiment, the network interface is bifurcated into a first network interface 506 for communicating with other server apparatuses and a second network interface 508 for communicating with user devices. Other implementations may combine these functionalities into a single network interface, the foregoing being purely illustrative.

In one exemplary embodiment, the first network interface 506 is a wide area network port that allows for communications with remote computers over the Internet (e.g., external databases). The first network interface 506 may further include a local area network port that enables communication with any of various local computers housed in the same or nearby facility. In at least one embodiment, the local area network port is equipped with a Wi-Fi transceiver or other wireless communications device. Accordingly, it will be appreciated that communications with the server 500 may occur via wired communications or via the wireless communications. Communications may be accomplished using any of various known communications protocols.

In one exemplary embodiment, the second network interface 508 is a network port that allows for communications with a population of health tracking user devices. The second network interface 508 may be configured to interface to a variety of different networking technologies consistent with consumer electronics. For example, the network port may communicate with a Wi-Fi network, cellular network, and/or Bluetooth devices.

In one exemplary embodiment, the server 500 is specifically configured to analyze workout data records from a number of users to generate expected profiles that describe e.g., the physiological and/or psychological behavior of similar users in terms of heuristics and performance metrics in accordance with the principles described above. In particular, the illustrated server apparatus 500 stores one or more computer-readable instructions that when executed enable e.g., analyze workout data records from a population of users to generate profiles, recommend workouts to users based on the profiles, and update workout data records with logged performance.

FIG. 5B is a logical block diagram of one exemplary user apparatus 550, useful in accordance with the various principles described herein. In one embodiment, the exemplary user apparatus 550 includes a processor 552, non-transitory computer-readable medium 554, a network interface 556, a user interface 558, and sensors 560.

In one exemplary embodiment, the user devices 550 are configured to monitor a user's workout progress and dynamically provide feedback in accordance with an expected profile. User devices 550 may also be referred to herein as health and/or activity monitoring devices, or client devices. The user devices 550, in one exemplary implementation, include one or more portable computerized devices that are configured to e.g., recommend, display, monitor, feedback, motivate, and/or otherwise provide workout information to a user. In an exemplary embodiment, the specific workout information that are displayed may include the exercise, current progress, expected progress, and/or any dynamic feedback associated therewith.

In one exemplary embodiment, the user devices 550 are additionally configured to enable a user to log actual workout activity. The user devices 550 may include one or more portable computerized devices that are configured to measure, obtain, monitor, generate, collect, sense, or otherwise receive physiological and/or psychological impact experienced by a user. In an exemplary embodiment, the specific data that are collected may include e.g., repetition count, set count, duration, as well as physiological information such as e.g., heart rate, blood oxygenation, carbon dioxide production, lactate production, blood occlusion, nervous system activation, sweat, blood sugar, etc.

In some embodiments, the user devices 550 may include a variety of sensors 560 including, without limitation: accelerometers, heart rate monitors, cameras, microphones and/or other sensing mechanisms (e.g., blood monitors, etc.) For example, a client device may use an accelerometer to e.g., count steps, repetitions, monitor motion (e.g, form). Similarly, blood oxygen sensors can detect e.g., blood oxygenation, lactate production, etc. Cameras can be used to monitor changes to form/body positioning (via video analysis), and microphones can be used to capture audible data (exhalations, foot strikes, etc.)

In one variant, certain ones of the user devices 550 may include wearable health-related parameter measurement and computing devices, such as e.g., a smart watch, an activity tracker, a heart rate monitor, a sleep tracking device, a smart scale, and/or smart eyeglasses. In addition, an exemplary user device 550 may include a smartphone having one or more of the foregoing capabilities and/or which enables user entry of the foregoing workout data. Alternatively, the user device 550 may be in communication with a health and/or activity monitoring device.

Other examples of health parameter data may include data that the particular device 550 is configured to collect (such as athletic activity, biometric information, and environmental data). For example, an activity tracking device may be configured to collect activity data such as steps taken, distance traveled, rate or pace of a run, and/or flights of stairs climbed, etc.; a heart rate monitor may be configured to collect heartbeat data; a sleep tracking device collects data relating to how much time a user/wearer spends sleeping; a nutrition tracking device collects data relating to food and drinks consumed by a user; a smart scale collects data relating to a body weight, body fat percentage, and/or body mass index (BMI), etc. Furthermore, a smartwatch and/or smartphone, may be utilized as an activity tracking device, a heart rate monitor, a sleep tracking device, and/or a nutrition tracking device. The user device 550 may comprise any of the foregoing types of devices and/or may receive collected data from a first device at one or more applications running on the user device 550.

The exemplary user device 550 may be further configured enable entry and/or display of collected data. In such instances, the exemplary user device 550 may run one or more applications configured to process (e.g., transform) the collected data. Exemplary applications include e.g., UA Record™, MapMyFitness®, MyFitnessPal®, Endomondo®, etc. each owned by the Assignee hereof. Other health activity related monitoring applications may additionally be utilized in connection with the present disclosure, such as those specifically designed to receive information from a particular type of health monitoring device (e.g., a $1^{st}$ party application which is published by the device manufacturer, or $2^{nd}$ party (trusted) or $3^{rd}$ party (untrusted) applications designed to work in conjunction therewith); the foregoing being merely representative of the general concepts of the present disclosure.

Additionally, in one exemplary embodiment the application(s) running at the user device 550 includes a workout coaching application that enables dynamic feedback in accordance with an expected profile. The workout coaching application enables a user to receive workout recommendations and/or log workout activity. As discussed in greater detail supra, the workout coaching application enables a user to manage their workout regimen via communication to and/or coordination with a network side application run at the health tracking server 500.

The above described system and method solves a technological problem common in industry practice related to individually tailoring workout recommendations for individual users with different physiological and/or psychological traits. The above-described system and method improves the functioning of the computer/device by recommending workouts to the user based on collecting workout data from a population of similarly situated individuals, and ensuring that the user can receive dynamic feedback in accordance with an expected performance.

Portions of the system and methods described herein may be implemented using one or more programs or suitable software code, such as the workout recommendation application on the health tracking device and the health tracking program on the server, both described above, each of which may reside within the memory of the respective computing devices as software or firmware. Such programs and code may be stored in the memory and executed by the processor of the display device or a system server or other computer in communication with the display device. A computer program product implementing an embodiment disclosed herein may therefore comprise one or more computer-readable storage media storing computer instructions translatable by processing circuitry/logic, a CPU, or other data processing device to provide an embodiment of a system or perform an embodiment of a method disclosed herein. Computer instructions may be provided by lines of code in any of various languages as will be recognized by those of ordinary skill in the art.

A "computer-readable medium" may be any type of data storage medium that can store computer instructions and/or data, including, read-only memory (ROM), random access memory (RAM), hard disks (HD), data cartridges, data backup magnetic tapes, floppy diskettes, flash memory, optical data storage, CD-ROMs, or the like. The computer-readable medium can be, by way of example, only but not by limitation, an electronic, magnetic, optical, electromagnetic, infrared, or semiconductor system, apparatus, system, device, or computer memory. The computer-readable medium may include multiple computer-readable media storing computer executable instructions, such as in a distributed system or instructions stored across an array. A "non-transient computer-readable medium" may be any type of data storage medium that can store computer instructions, including, but not limited to the memory devices discussed above.

FIGS. 6A-6D depict graphical representations of an exemplary user interface, consistent with the various principles described herein.

FIG. 6A illustrates a user interface for requesting user input regarding their personal fitness goals during onboarding. The user input can be used for initial assessment, baselining, and profile construction. In some cases, the information enables the health and fitness tracking system to tailor content and target products that users are interested in.

FIG. 6B illustrates a user interface which identifies user parameters determined during an initial assessment/baseline and/or subsequent exercises. The illustrated embodiment shows an exercise and relevant measured performance metrics (e.g., performance per muscle group, etc.)

FIG. 6C illustrates a user interface which dynamically generates a workout based on e.g., physiological and/or psychological user input. Specifically, a workout is generated based on readiness inputs, current location, and workout schedule. The workout intensity may be modified based on readiness inputs and past rate of perceived effort (RPE) inputs. The workout length may be adjusted to complete before upcoming events in the user's calendar. Location information may be used to recommend exercises based on the available equipment at the workout location.

Figure 6D:
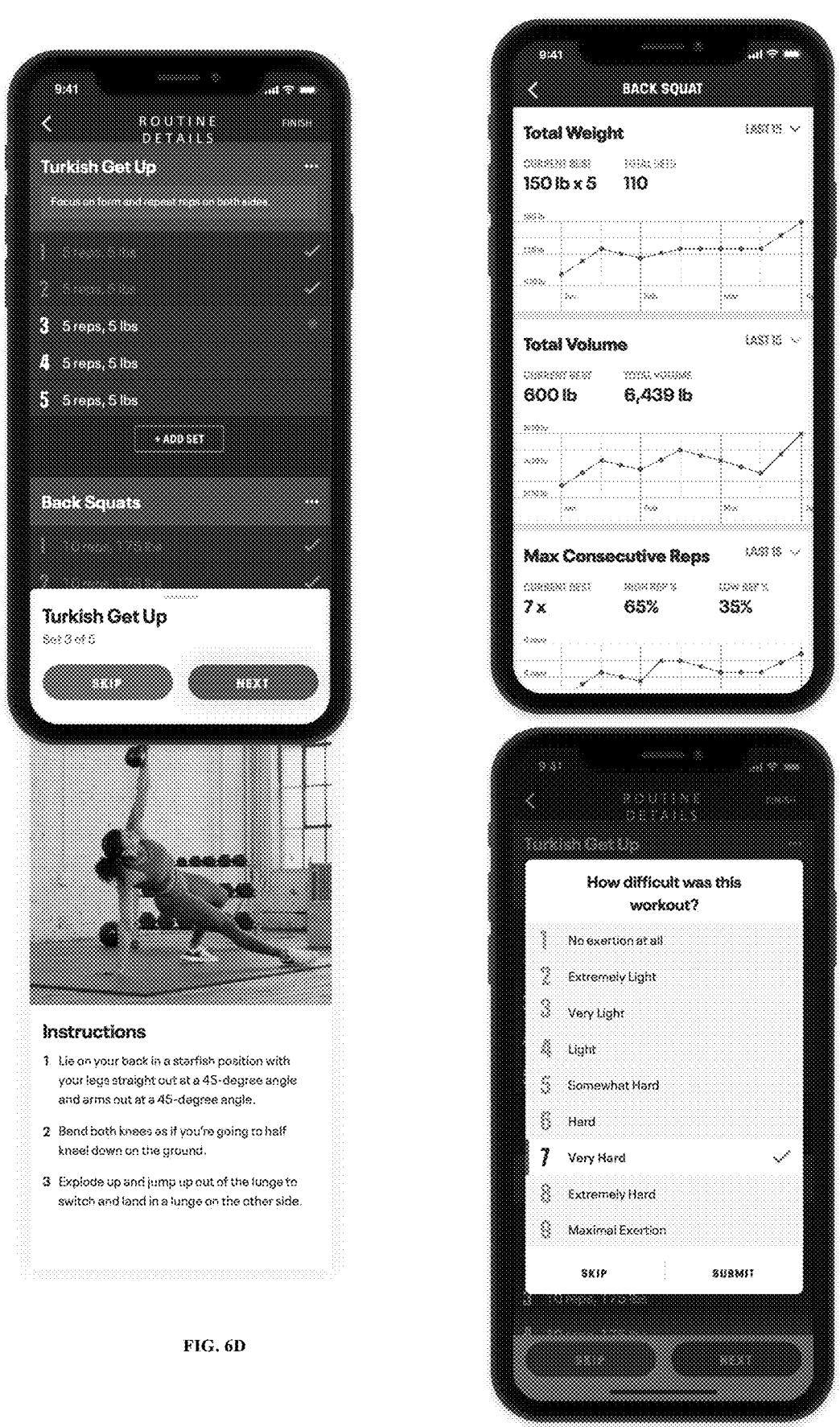

FIG. 6D illustrates a user interface which recommends and provides dynamic feedback to users during their workout regimen. The interface provides informative references for the exercise, and visual indication on routine progress. During the workout, the user is prompted to provide Rate of Perceived Effort (RPE) feedback along the way. RPE can be used to provide dynamic feedback as well as improve future workout recommendations.

In the foregoing description, various operations may be described as multiple discrete actions or operations in turn, in a manner that may be helpful in understanding the claimed subject matter. However, the order of description should not be construed as to imply that these operations are necessarily order dependent. In particular, these operations may not be performed in the order of presentation. Operations described may be performed in a different order than the described embodiment. Various additional operations may be performed and/or described operations may be omitted in additional embodiments.

The foregoing detailed description of one or more exemplary embodiments of the health tracking system with workout coaching has been presented herein by way of example only and not limitation. It will be recognized that there are advantages to certain individual features and functions described herein that may be obtained without incorporating other features and functions described herein. Moreover, it will be recognized that various alternatives, modifications, variations, or improvements of the above-disclosed exemplary embodiments and other features and functions, or alternatives thereof, may be desirably combined into many other different embodiments, systems or applications. Presently unforeseen or unanticipated alternatives, modifications, variations, or improvements therein may be subsequently made by those skilled in the art which are also intended to be encompassed by the appended claims. Therefore, the spirit and scope of any appended claims should not be limited to the description of the exemplary embodiments contained herein.

In another embodiment, a permanent copy of the programming instructions for individual ones of the aforementioned applications may be placed into permanent storage devices (such as e.g., memory) during manufacture thereof, or in the field, through e.g., a distribution medium (not shown), such as a compact disc (CD), or through communication interface (from a distribution server). That is, one or more distribution media having an implementation of the agent program may be employed to distribute the agent and program various computing devices.

It will be appreciated that the various ones of the foregoing aspects of the present disclosure, or any parts or functions thereof, may be implemented using hardware, software, firmware, tangible, and non-transitory computer-readable or computer usable storage media having instructions stored thereon, or a combination thereof, and may be implemented in one or more computer systems.

It will be apparent to those skilled in the art that various modifications and variations can be made in the disclosed embodiments of the disclosed device and associated methods without departing from the spirit or scope of the disclosure. Thus, it is intended that the present disclosure covers the modifications and variations of the embodiments disclosed above provided that the modifications and variations come within the scope of any claims and their equivalents.

What is claimed is:

1. A method for enabling dynamic coaching feedback at a client device, comprising:
    generating a plurality of expected profiles for a plurality of data records within a user workout history database by:
        using a supervised machine learning model to group users into the plurality of expected profiles; and
        using unsupervised machine learning to generate heuristics and performance metrics for each of the plurality of expected profiles;
    associating a first user with one of the expected profiles;
    receiving user input from the first user relating to at least one workout;
    in response to receiving the user input, recommending a workout for the first user based on the expected profile associated with the first user;
    wherein the expected profile associated with the first user includes at least one heuristic for generating dynamic feedback with the workout, wherein the at least one heuristic for generating the dynamic feedback comprises a rule for modifying a second exercise of the workout based on an actual performance of a first exercise of the workout, wherein the expected profile comprises an expected performance level for the first exercise of the workout, and wherein said expected performance level is based on a model profile taken from a subset of users identified as having a similar physiology and similar psychology as the first user; and
    updating a user data record of the first user based on a logged performance corresponding to the at least one workout.

2. The method of claim 1, where the workout data records are obtained from a population of users.

3. The method of claim 2, wherein the population of users are categorized based on at least one physiological or psychological trait.

4. The method of claim 1, where the at least one heuristic for generating the dynamic feedback comprises a rule for motivating the user based on an actual performance of the first exercise of the workout.

5. The method of claim 1, further comprising identifying the expected profile from the plurality of expected profiles based at least in part on an assessment performance, the method further comprising disassociating the first use with the expected profile and associating the user with a different one of the plurality of expected profiles based at least in part on the logged performance.

6. The method of claim 1 wherein the similar psychology is one or more of a similar confidence state, motivational state, or emotional state.

7. A health tracking server configured to recommend workout to users, comprising:
    a network interface;
    a processor;
    a non-transitory computer-readable medium comprising one or more instructions, which when executed by the processor, causes the health tracking server to:
        obtain workout data records associated with users;
        analyze the workout data records to group the users into a plurality of distinct subsets, wherein the users are grouped into the subsets based on machine learning data analysis of physiological and psychological traits;
        analyze each subset to generate a corresponding model profile for each subset, each model profile comprising at least a heuristic and a performance metric associated therewith, wherein the at least one heuristic is a heuristic for generating dynamic feedback comprising a rule for modifying a second exercise of a workout based on an actual performance of a first exercise of the workout;
        receive user input from a user device relating to at least one first exercise of a workout of a first user;
        match the first user with a first model profile based at least in part on said received user input relating to at least one first exercise;
        recommend to the first user a modification to at least one second exercise of the workout of the first user based on the first model profile, wherein the modification is recommended responsive to said user input;

receive subsequent user input from the user device relating to the at least one second exercise of the workout of the first user; and based at least in part on the received user input and subsequent user input, use machine learning to identify a pattern of the first user that identifies the first user with a second model profile; and match the first user with the second model profile.

8. The health tracking server of claim 7, wherein the corresponding model profile for each subset is generated based on machine learning data analysis of physiological and psychological traits.

9. The health tracking server of claim 7, wherein the first user is matched with the first profile from a plurality of profiles based at least in part on an assessment exercise.

10. The health tracking server of claim 7, wherein the first user is matched with the first profile from a plurality of profiles based at least in part on a history of user workout data records.

11. The health tracking server of claim 7, where in the first user is matched with the first profile from a plurality of profiles based at least in part on a fitness goal identified by the first user.

12. The health tracking server of claim 7 the psychological traits include one or more of an assessed confidence, motivation or emotional state.

13. A user apparatus, comprising:
a user interface configured to receive user input related to a workout performed by a user;
a network interface configured to transmit the user input to a health tracking server;
a processor; and
a non-transitory computer-readable medium comprising one or more instructions, which when executed by the processor, causes the user apparatus to:
receive a first recommended workout and a first model profile comprising a performance metric for a first exercise of a workout, wherein the performance metric includes least one heuristic for generating dynamic feedback for modifying a second exercise of the workout based on an actual performance of the first exercise of the workout, and wherein said recommended workout is received from a health tracking server configured to:
(i) match the user with the first model profile based at least in part on said user input related to the workout performed by the user; and
(ii) generate said recommended workout responsive to said user input;
(iii) use machine learning to identify a pattern of the user that identifies the user with a second model profile; and
(iv) match the user with the second model profile;
monitor performance during the recommended workout;
when the performance does not match the performance metric for the first exercise, provide dynamic feedback for the second exercise based on the first user profile; and
receive a second recommended workout and the second model profile.

14. The user apparatus of claim 13, wherein the recommended workout is selected from a plurality of recommended workouts.

15. The user apparatus of claim 13, wherein the first user profile and second user profile are matched for the user associated with the user apparatus.

16. The user apparatus of claim 13, wherein the dynamic feedback comprises a revised workout.

17. The user apparatus of claim 16, wherein the one or more instructions, when executed by the processor, causes the user apparatus to log a revised performance with the revised workout.

18. The user apparatus of claim 13, wherein the dynamic feedback comprises a motivational message.

* * * * *